United States Patent [19]
Daugan et al.

[11] Patent Number: 6,143,757
[45] Date of Patent: *Nov. 7, 2000

[54] CHEMICAL COMPOUNDS

[75] Inventors: Alain Claude-Marie Daugan, Marly le Roi Cedex, France; Richard Frederick LaBaudiniere, Collegeville, Pa.

[73] Assignee: ICOS Corporation, Bothell, Wash.

[*] Notice: This patent is subject to a terminal disclaimer.

[21] Appl. No.: 09/154,619

[22] Filed: Sep. 16, 1998

Related U.S. Application Data

[63] Continuation-in-part of application No. PCT/EP96/03023, Jul. 11, 1996.

[51] Int. Cl.$^7$ ................................................. A61K 31/44
[52] U.S. Cl. ................... 514/285; 514/277; 514/279; 514/284; 514/287; 514/359
[58] Field of Search .................. 514/277, 279, 514/284, 285, 287, 359

[56] References Cited

U.S. PATENT DOCUMENTS

| | | | |
|---|---|---|---|
| 3,644,384 | 2/1972 | Schulenberg | 260/295 C |
| 3,717,638 | 2/1973 | Schulenberg | 260/268 PC |
| 3,917,599 | 11/1975 | Saxena et al. | 260/268 PC |
| 4,188,390 | 2/1980 | Campbell | 424/251 |
| 4,686,228 | 8/1987 | Campbell et al. | 514/307 |
| 4,801,587 | 1/1989 | Voss et al. | 514/248 |
| 5,145,852 | 9/1992 | Virag | 514/253 |
| 5,270,323 | 12/1993 | Milne, Jr. et al. | 514/309 |
| 5,770,606 | 6/1998 | El-Rashidy et al. | 514/284 |
| 5,859,006 | 1/1999 | Daugan | 514/249 |
| 5,874,437 | 2/1999 | Garvey et al. | 514/258 |
| 5,981,527 | 11/1999 | Daugan et al. | 514/250 |

FOREIGN PATENT DOCUMENTS

| | | |
|---|---|---|
| 0 357 122 | 7/1990 | European Pat. Off. . |
| 0 362 555 | 11/1990 | European Pat. Off. . |
| 459 666 | 12/1991 | European Pat. Off. . |
| 463 756 | 1/1992 | European Pat. Off. . |
| 526 004 | 2/1993 | European Pat. Off. . |
| 030443224 | 2/1991 | Japan . |
| 1454171 | 10/1976 | United Kingdom . |
| WO 89/10123 | 2/1989 | WIPO . |
| WO 94/05661 | 3/1994 | WIPO . |
| WO 94/28902 | 12/1994 | WIPO . |
| WO 95/19978 | 7/1995 | WIPO . |

OTHER PUBLICATIONS

A. Bowman et al., *Br. J. Pharmac.*, (1984), 81, 665–674.
F. Trigo–Rocha et al., *Am. J. Physiol.*, (Feb. 1993), 264, H419–H422.
J. Reiser et al., *Br. J. Dis. Chest*, (1986), 80, 157–163.
P. Bush et al., *J. Urol.*, (Jun. 1992), 147, 1650–1655.
F. Holmquist et al., *J. Urol.* (Oct. 1993), 150, 1310–1315.
R. Rudd et al., *Br. J. Dis. Chest*, (1983), 77, 78–86.
E. McMahon et al., *J. Pharmacol. Exp. Thera.*, (1989), 251, 1000–1005.
F. Holmquist et al., *Acta Physiol. Scand.*, (1991), 143, 299–304.
G. Barbanti *Urol. Res.*, (1988), 16, 299–302.
L. Ignarro et al., *Biochem. and Biophys. Res. Commun.*, (1990), 170(2), 843–850.
J. Krall et al., *Bio. Reprod.*, (1988), 39, 913–922.
M. Wilkins et al., *Proc. Natl. Acad. Sci., USA*, (Aug. 1990), 87, 6465–6469.
M. Wilkins et al., *J. Clin. Invest.*, (Apr. 1990), 85, 1274–1279.
J. Rajfer, *N. Eng. J. Med.*, (Jan. 1992), 326(2), 90–94.
H. Knispel, *Urol. Res.*, (1992), 20, 253–257.
G. Gwinup, *Annals. of Internal Medicine*, (Jul. 1988), 162–163.
Z. Zorgniotti, *J. Urol.*, (Apr. 1992), 147(4), 308A.
K. Azadzoi et al., *J. Urol.*, (Nov. 1992), 148, 1587–1591.
K. Azadzoi et al., *J. Urol.*, (Jan. 1992), 147, 220–225.
C. Sparwasser et al., *J. Urol.*, (Dec. 1994), 152, 2159–2163.
T. Lue, "Campbell's Urology," 6th Ed., Chap. 16, P. Walsh et al., Eds., W.B. Saunders Co., 709–728 (1991).
N. Kim et al., *J. Clin. Invest.*, (1991), 88, 112–118.
S. Francis et al., in J. Beavo et al. eds. "Cyclic Nucleotide PDEs" Ch. 5 (1990) 117–140.
R. Weishaar et al., *J. Med. Chem.*, (1985), 28:5, 537–542.
H. Ahn et al., *Biochem. Pharmacol.*, (1989), 39:19, 3331–3339.
C. Lugnier et al., *Biochem. Pharmacol.*, (1986), 35:10, 1743–1751.
J. Doremieux et al., *Ann. Urol. Paris*, (1987), 21(6), 429–434.
D. Green et al., *Geriatrics*, (Jan. 1993), 48(1), 46–58.
M. Webster et al., *Hematol. Oncol. Cl. of N. Am.*, (Feb. 1990), 4(1), 265–289.
F. Holmquist et al., *Acta. Physiol. Scand.*, (1991), 141, 441–442.
J. Taher et al., *J. Urol.*, (Apr. 1993), 149, 285A.
S. Uckert et al., *J. Urol.*, 151 (5 Supp.), (1994), 495A.
W. Aronson et al., *J. Urol.*, (1991), 145 (4 Supp.), 341A.
P. Bush et al., *Fed. Am. Soc. Exp. Biol.*, (1991), 5(4), 175.
P. Bush et al., *Fed. Am. Soc. Exp. Biol.*, (1992), 6(4), 2092.
W. Aronson et al., *J. Urol.*, (1992), 147 (4 Supp.), 454A.
P. Bush et al., *Circulation*, (May 1993), 87 Supp. V, V–30–V–32.

(List continued on next page.)

*Primary Examiner*—Marianne M. Cintins
*Assistant Examiner*—C Delacroix-Muirhead
*Attorney, Agent, or Firm*—Marshall, O'Toole, Gerstein, Murray & Borun

[57] ABSTRACT

Compounds of the general structural formula

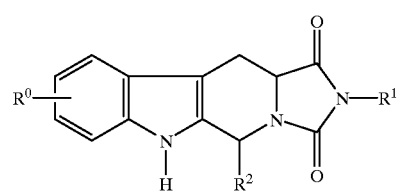

and use of the compounds and salts and solvates thereof, as therapeutic agents.

13 Claims, No Drawings

OTHER PUBLICATIONS

R. Pickard et al., *J. Urol.,* (May 1993), 149 (4 Supp.), 245A.
R. Pickard et al., *Clin. Pharmacol.,* (Jan. 1993), 35(5), 536P–537P.
F. Trigo–Rocha et al., *J. Urol.,* (Apr. 1993), 149, 872–877.
M. Krupp et al., *J. Cardiovas. Pharmacol.,* (1989), 13 (Supp.2), S11–S19.
"Physicians' Desk Reference," (1992), 683, 1099–1100, 1344, 1941–1943.
R. Morales et al., *World J. Urol.,* (1990), 8, 80–83.
J. Cortijo, *Br. J. Pharmacol.,* (Feb. 1993), 108(2), 562–568.
E. Kim et al., *J. Urol.,* (1995), 153, 361–365.
S. Korenman et al., *JAGS,* (Apr. 1993), 41(4), 363–366.
K. Allenby et al., *Angiology,* (1991), 42, 418–420.
H. Hamilton et al., *J. Med. Chem.,* (1987), 30, 91–96.
H. Padma–Nathan et al., *Sem. in Urol.,* (Nov. 1986), vol. IV, No. 4, 236–238.
J. Beavo et al., *TiPS,* (Apr. 1990), 11, 150–155.
S. Korenman et al., *Clin. Res.,* (1988), 36, 123A.
D. Halsted et al., *J. Urol.,* (Jul. 1986), 136, 109–110.
W. Thompson, *Pharmac. Ther.,* (1991), 51, 13–33.
M. Giembycz et al., *Clin. and Exper. Allergy,* (1992), 22, 337–344.
C. Nicholson et al., *TIPS,* (Jan. 1991), 12, 19–27.
J. LeBlanc et al., *Eur. J. Cardiothorac Surg.,* (1993), 7, 211–215.
C. Stief et al., *J. Urol.,* (Nov. 1992), 148, 1437–1440.
C. Stief et al., *World J. Urol.,* (1991), 9, 237–239.
C. Clyne et al., *Br. J. Surg.,* (Apr. 1987), 74, 246–248.
V. Mirone et al., *Acta Urol. Ltd.,* (1992), Suppl. 4, 11–12.
P. Bush, Ph.D. Thesis (1992), pp. 159–160.
T. Lincoln, *Pharmac. Ther.,* (1989), 41, 479–502.
J. Heaton et al., *Urology,* (Feb. 1995), 45(2), 200–206.
Saxena et al., *Journal of Medicinal Chemistry,* vol. 16, No. 5, 560–564 (1973).
Ishida et al., *Chem. Pharm. Bull.,* vol. 33, No. 8, 3237–3249 (1985).
Gillespie et al., *Molecular Pharmacology,* 36:773–781 (1989).
Braña et al., *Synthetic Communications,* 20(12), 1793–1820 (1990).
Dellouve–Courillon et al., *Tetrahedron,* 46, No. 9, 3245–3266 (1990).
Murray, *DN&P 6(3),* 150–156 (1993).
Zorgniotti et al. *Int. J. Impotence Res.,* 6, 33–36 (1994).
Beyer et al., *Phys. and Behav.,* (1981), 27, 731–733.
Pickard et al., *Br. J. Pharmacol.,* (1991), 104 755–759.
Martinez–Pineiro et al., *Eur. Urol.,* (1992), 24, 492–499.
Mirone et al., *Br. J. Urol.,* (Mar. 1993), 71(3), 365.
Murray et al., *Biochemical Soc. Trans.,* (1992), 20, 460–464.
Raeburn et al., *Prog. Drug Res.,* (1993), 12–32.
Merkel, *Cardio. Drug. Rev.,* (1993), 11(4), 501–515.
"Physicians' Desk Reference," (1992), 2207–2208.
Cimino et al., *Biochem. Pharmacology,* (1988), 37(14), 2739–2745.
Watanabe et al., *Federation Proceedings,* (1982), 41(7), 2292–2399.
Earl et al., *Life Sciences,* (1984), 35, 525–534.
Brindley, *Brit. J. Phychiat.,* (1993), 143, 332–337.
Keogh, *Aust. NZ. J. Med.,* (1989), 19, 108–112.
Funderbunk, *New Engl. J. Med.,* (1974), 290, 630–631.
Beretta, *Acta European Fertilitatis,* (1986), 17, 43–45.
"Physicians' Desk Reference," (1992), 1778–1779.
Hess in "Prazosin: Evaluation of a New Antihypertensive Agent," D. Cotton ed., American Elsevier, NY, (1974), 3–15.
Dadkar et al., *Ind. J. Exp. Biol.,* (1982), 20, 484–487.
D'Armiento et al., *Eur. J. Pharmacol.,* (1980), 65, 234–247.
Bhalla et al., *Brit. Med. J.,* (1979), 2, 1059.
Burke et al., *Med. J. Aust.,* (1980), 382–383.
Segasouthy et al., *Med. J. Malaysia,* (1982), 37(4), 384.
Ylitalo et al., *Acta Med. Scand.,* (1983), 213, 319–320.
Robbins et al., *J. Urol.,* (1983), 130, 975.
Adams et al., *J. Urol.,* (1984), 132, 1208.
Russell et al., *Med. J. Aust.,* (1985), 143, 321.
Taher et al., *Int. J. Impotence Res.,* Abstracts, Milan, Italy (Sep. 14–17, 1992).
Trigo–Rocha et al., *Neurology and Urodynamics,* 13, (1998) 71–80.
Lopez–Rodriguez et al., *Chemical and Pharmaceutical Bulletin,* vol. 43, No. 6 (Jun. 1995) pp. 941–946.
Miguel et al., *Journal of Heterocyclic Chemistry,* vol. 31, No. 5 (1994) pp. 1235–1239.
Lopez–Rodriguez et al., *Journal of Organic Chemistry,* vol. 59, No. 6 (1994) pp. 1583–1595.
Braña et al., *Journal of Heterocyclic Chemistry,* vol. 27, No. 3 (1990) pp. 703–706.
Sandrin et al., *Heterocycles,* vol. 4, No. 7 (1976) pp. 1249–1255.
Braña et al., *Liebigs Annalen der Chemie,* No. 8, (1992) pp. 867–869.

CHEMICAL COMPOUNDS

CROSS-REFERENCE TO RELATED APPLICATIONS

This is a continuation-in-part application of PCT Application Serial No. PCT/EP96/03023 (U.S. Ser. No. 08/981,966), filed Jul. 11, 1996.

FIELD AND BACKGROUND OF THE INVENTION

This invention relates to a series of tetracyclic derivatives, processes for their preparation, pharmaceutical compositions containing them, and their use as therapeutic agents. In particular, the invention relates to tetracyclic derivatives which are potent and selective inhibitors of cyclic guanosine 3',5'-monophosphate specific phosphodiesterase (cGMP-specific PDE) having utility in a variety of therapeutic areas where such inhibition is thought to be beneficial, including the treatment of cardiovascular disorders and erectile dysfunction.

SUMMARY OF THE INVENTION

The present invention provides compounds of formula (I)

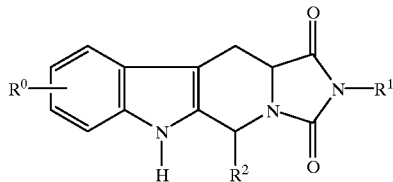

and pharmaceutically acceptable salts and solvates (e.g., hydrates) thereof, in which:

$R^0$ represents hydrogen, halogen, or $C_{1-6}$alkyl;

$R^1$ is selected from the group consisting of:
(a) hydrogen,
(b) $C_{1-6}$alkyl, optionally substituted with one or more substituents selected from phenyl, halogen, —$CO_2R^a$ and —$NR^aR^b$,
(c) $C_{3-6}$cycloalkyl,
(d) phenyl, and
(e) a 5- or 6-membered heterocyclic ring containing at least one heteroatom selected from oxygen, nitrogen and sulphur, and being optionally substituted with one or more $C_{1-6}$alkyl, and optionally linked to the nitrogen atom to which $R^1$ is attached via $C_{1-6}$alkyl;

$R^2$ is selected from the group consisting of:
(f) $C_{3-6}$cycloalkyl,
(g) phenyl, optionally substituted with one or more substituents selected from —$OR^a$, —$NR^aR^b$, halogen, hydroxy, trifluoromethyl, cyano, and nitro,
(h) a 5- or 6-membered heterocyclic ring containing at least one heteroatom selected from oxygen, nitrogen and sulphur; and
(i) a bicyclic ring

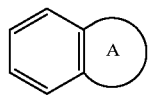

attached to the rest of the molecule via one of the benzene ring carbon atoms, wherein A is a 5- or 6-membered heterocyclic ring as defined in (h); and $R^a$ and $R^b$, independently, represent hydrogen or $C_{1-6}$alkyl.

The term "$C_{1-6}$alkyl" as used herein denotes any straight or branched alkyl chain containing 1 to 6 carbon atoms, and includes methyl, ethyl, n-propyl, iso-propyl, n-butyl, pentyl, hexyl, and the like.

The term "halogen" as used herein denotes fluorine, chlorine, bromine, and iodine.

A particular group of compounds according to formula (I) are those wherein $R^0$ represents any of hydrogen, methyl, bromine, and fluorine, but the definition of $R^0$ given in formula (I) includes within its scope other $C_{1-6}$-alkyl and halogen groups.

$R^1$ can represent a substituent selected from methyl, ethyl (optionally substituted by one or more chlorine atoms), butyl, cyclohexyl and benzyl. Other $R^1$ substituents include hydrogen; cycloalkyl groups, such as cyclopropyl; $C_{1-6}$alkyl, typically ethyl or propyl, substituted by an —$NR^aR^b$ substituent, such as a dimethylamino substituent; phenyl optionally linked to the nitrogen atom to which $R^1$ is attached via a $C_{1-6}$alkyl chain, such as ethyl or the like; and $C_{1-6}$alkyl, e.g., methyl, substituted by —$CO_2R^a$, such as —$CH_2CO_2Et$ (Et is $CH_2CH_3$) and the like.

Suitable heterocyclic rings within the definition of $R^1$ include pyridyl, morpholinyl, piperazinyl, pyrrolidinyl, and piperidinyl. Generally, such heterocyclic rings are linked to the nitrogen atom to which $R^1$ is attached via a $C_{1-6}$alkyl chain, more appropriately a $C_{1-4}$alkyl chain.

A particular substituent represented by $R^2$ is

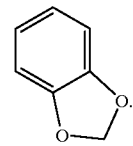

Other $R^2$ substituents include thienyl, pyridyl, furyl, and phenyl, wherein phenyl can be substituted with one or more substituents selected from —$OR^a$ (e.g., methoxy), —$NR^aR^b$ (e.g., dimethylamino), halogen (in particular chlorine or fluorine), hydroxy, trifluoromethyl, cyano, and nitro. Alternatively, $R^2$ can represent a $C_{3-6}$cycloalkyl group, such as cyclohexyl or the like.

The pharmaceutically acceptable salts of the compounds of formula (I) that contain a basic center are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulphonate, benzenesulphonate, and p-toluenesulphonate salts. Compounds of formula (I) also can provide pharmaceutically acceptable metal salts, in particular alkali metal salts, with bases. Examples include the sodium and potassium salts.

It is to be understood that the present invention covers all appropriate combinations of particular and preferred groupings hereinabove.

Particular individual compounds of the invention include:

Cis-2-benzyl-5-(3,4-methylenedioxyphenyl)-5,6,11,11a-tetrahydro-1H-imidazo[1',5':1,6]pyrido[3,4-b]indole-1,3(2H)-dione;

Trans-2-benzyl-5-(3,4-methylenedioxyphenyl)-5,6,11,11a-tetrahydro-1H-imidazo[1',5':1,6]pyrido[3,4-b]indole-1,3(2H)-dione;

Cis-5-(4-methoxyphenyl)-2-methyl-5,6,11,11a-tetrahydro-1H-imidazo[1',5':1,6]pyrido[3,4-b]indole-1,3(2H)-dione;

Cis-2-ethyl-5-(4-methoxyphenyl)-5,6,11,11a-tetrahydro-1H-imidazo[1',5':1,6]pyrido[3,4-b]indole-1,3(2H)-dione;

Trans-2-ethyl-5-(4-methoxyphenyl)-5,6,11,11a-tetrahydro-1H-imidazo[1',5':1,6]pyrido[3,4-b]indole-1,3(2H)-dione;

Trans-2-ethyl-5-(3,4-methylenedioxyphenyl)-5,6,11,11a-tetrahydro-1H-imidazo [1',5':1,6]pyrido[3,4-b]indole-1,3(2H)-dione;

Trans-2-ethyl-5-(2-thienyl)-5,6,11,11a-tetrahydro-1H-imidazo-[1',5':1,6]pyrido[3,4-b]indole-1,3(2H)-dione;

Trans-5-(4-dimethylaminophenyl)-2-ethyl-5,6,11,11a-tetrahydro-1H-imidazo[1',5':1,6]pyrido[3,4-b]indole-1,3(2H)-dione;

Trans-2-butyl-9-methyl-5-phenyl-5,6,11,11a-tetrahydro-1H-imidazo[1',5':1,6]pyrido[3,4-b]indole-1,3(2H)-dione;

Trans-9-bromo-2-butyl-5-phenyl-5,6,11,11a-tetrahydro-1H-imidazo[1',5':1,6]pyrido[3,4-b]indole-1,3(2H)-dione;

Cis-2-butyl-5-(4-methoxyphenyl)-5,6,11,11a-tetrahydro-1H-imidazo[1',5':1,6]pyrido[3,4-b]indole-1,3(2H)-dione;

Trans-2-butyl-5-(4-methoxyphenyl)-5,6,11,11a-tetrahydro-1H-imidazo [1',5':1,6]pyrido[3,4-b]indole-1,3(2H)-dione;

Cis-2-butyl-9-fluoro-5-(4-methoxyphenyl)-5,6,11,11a-tetrahydro-1H-imidazo [1',5':1,6]pyrido[3,4-b]indole-1,3(2H)-dione;

Trans-2-butyl-9-fluoro-5-(4-methoxyphenyl)-5,6,11,11a-tetrahydro-1H-imidazo[1',5':1,6]pyrido[3,4-b]indole-1,3(2H)-dione;

Trans-2-butyl-5-(3,4-methylenedioxyphenyl)-5,6,11,11a-tetrahydro-1H-imidazo[1',5':1,6]pyrido[3,4-b]indole-1,3(2H)-dione;

Cis-2-butyl-5-(3-chlorophenyl)-5,6,11,11a-tetrahydro-1H-imidazo[1',5':1,6]pyrido[3,4-b]indole-1,3(2H)-dione;

Trans-2-butyl-5-(3-chlorophenyl)-5,6,11,11a-tetrahydro-1H-imidazo[1',5':1,6]pyrido[3,4-b]indole-1,3(2H)-dione;

Cis-2-butyl-5-(4-chlorophenyl)-5,6,11,11a-tetrahydro-1H-imidazo[1',5':1,6]pyrido[3,4-b]indole-1,3(2H)-dione;

Trans-2-butyl-5-(4-chlorophenyl)-5,6,11,11a-tetrahydro-1H-imidazo[1',5':1,6]pyrido[3,4-b]indole-1,3(2H)-dione;

Trans-2-butyl-5-(4-fluorophenyl)-5,6,11,11a-tetrahydro-1H-imidazo[1',5':1,6]pyrido[3,4-b]indole-1,3(2H)-dione;

Trans-2-butyl-5-(4-hydroxyphenyl)-5,6,11,11a-tetrahydro-1H-imidazo[1', 5':1,6]pyrido[3,4-b]indole-1,3(2H)-dione;

Cis-2-butyl-5-(4-trifluoromethylphenyl)-5,6,11,11a-tetrahydro-1H-imidazo-[1',5':1,6]pyrido[3,4-b]indole-1,3(2H)-dione;

Cis-2-butyl-5-(4-cyanophenyl)-5,6,11,11a-tetrahydro-1H-imidazo[1',5':1,6]pyrido[3,4-b]indole-1,3(2H)-dione;

Trans-2-butyl-5-(4-cyanophenyl)-5,6,11,11a-tetrahydro-1H-imidazo[1',5':1,6]pyrido[3,4-b]indole-1,3(2H)-dione;

Cis-2-butyl-5-(4-nitrophenyl)-5,6,11,11a-tetrahydro-1H-imidazo[1',5':1,6]pyrido[3,4-b]indole-1,3(2H)-dione;

Trans-2-butyl-5-(4-nitrophenyl)-5,6,11,11a-tetrahydro-1H-imidazo[1',5':1,6]pyrido[3,4-b]indole-1,3(2H)-dione;

Cis-2-butyl-5-(3-pyridyl)-5,6,11,11a-tetrahydro-1H-imidazo[1',5':1,6]pyrido[3,4-b]indole-1,3(2H)-dione;

Cis-2-butyl-5-(3-thienyl)-5,6,11,11a-tetrahydro-1H-imidazo[1',5':1,6]pyrido[3,4-b]indole-1,3(2H)-dione;

Trans-2-butyl-5-(3-thienyl)-5,6,11,11a-tetrahydro-1H-imidazo[1',5':1,6]pyrido[3,4-b]indole-1,3(2H)-dione;

Cis-2-butyl-5-(3-furyl)-5,6,11,11a-tetrahydro-1H-imidazo[1',5':1,6]pyrido[3,4-b]indole-1,3(2H)-dione;

Trans-2-butyl-5-(3-furyl)-5,6,11,11a-tetrahydro-1H-imidazo[1',5':1,6]pyrido[3,4-b]indole-1,3(2H)-dione;

Cis-2-cyclohexyl-5-(4-methoxyphenyl)-5,6,11,11a-tetrahydro-1H-imidazo[1',5':1,6]pyrido[3,4-b]indole-1,3(2H)-dione;

Trans-2-cyclohexyl-5-(4-methoxyphenyl)-5,6,11,11a-tetrahydro-1H-imidazo[1',5':1,6]pyrido[3,4-b]indole-1,3(2H)-dione;

Cis-2-cyclohexyl-9-fluoro-5-(4-methoxyphenyl)-5,6,11,11a-tetrahydro-1H-imidazo[1',5':1,6]pyrido[3,4-b]indole-1,3(2H)-dione;

Trans-2-cyclohexyl-9-fluoro-5-(4-methoxyphenyl)-5,6,11,11a-tetrahydro-1H-imidazo[1',5':1,6]pyrido[3,4-b]indole-1,3(2H)-dione;

Trans-2-benzyl-5-phenyl-5,6,11,11a-tetrahydro-1H-imidazo [1',5':1,6]pyrido[3,4-b]indole-1,3(2H)-dione;

Cis-2-benzyl-5-(4-methoxyphenyl)-5,6,11,11a-tetrahydro-1H-imidazo[1',5':1,6]pyrido[3,4-b]indole-1,3(2H)-dione;

Trans-2-benzyl-5-(4-methoxyphenyl)-5,6,11,11a-tetrahydro-1H-imidazo[1', 5':1,6]pyrido[3,4-b]indole-1,3(2H)-dione;

(5R,11aR)-2-benzyl-5-(3,4-methylenedioxyphenyl)-5,6,11,11a-tetrahydro-1H-imidazo[1',5':1,6]pyrido[3,4-b]indole-1,3(2H)-dione;

Trans-2-benzyl-5-(4-hydroxyphenyl)-5,6,11,11a-tetrahydro-1H-imidazo[1',5':1,6]pyrido[3,4-b]indole-1,3(2H)-dione;

Trans-2-(2-chloroethyl)-5-(4-methoxyphenyl)-5,6,11,11a-tetrahydro-1H-imidazo[1',5':1,6]pyrido[3,4-b]indole-1,3(2H)-dione;

Cis-2-benzyl-5-cyclohexyl-5,6,11,11a-tetrahydro-1H-imidazo[1',5':1,6]pyrido[3,4-b]indole-1,3(2H)-dione;

Trans-2-benzyl-5-cyclohexyl-5,6,11,11a-tetrahydro-1H-imidazo[1',5':1,6]pyrido[3,4-b]indole-1,3(2H)-dione;

Trans-2-butyl-5-phenyl-5,6,11,11a-tetrahydro-1H-imidazo [1',5':1,6]pyrido[3,4-b]indole-1,3(2H)-dione;

Trans-2-cyclohexyl-5-phenyl-5,6,11,11a-tetrahydro-1H-imidazo[1',5':1,6]pyrido[3,4-b]indole-1,3(2H)-dione;

Cis-2-cyclohexyl-5-phenyl-5,6,11,11a-tetrahydro-1H-imidazo[1',5':1,6]pyrido[3,4-b]indole-1,3(2H)-dione;

Trans-2-ethoxycarbonylmethyl-5-(4-methoxyphenyl)-5,6,11,11a-tetrahydro-1H-imidazo[1',5':1,6]pyrido[3,4-b]indole-1,3(2H)-dione;

Trans-5-(4-methoxyphenyl)-2-[2-(2-pyridyl)-ethyl]5,6,11,11a-tetrahydro-1H-imidazo[1',5':1,6]pyrido[3,4-b]indole-1,3(2H)-dione;

Trans-2-cyclopropyl-5-phenyl-5,6,11,11a-tetrahydro-1H-imidazo[1',5':1,6]pyrido[3,4-b]indole-1,3(2H)-dione;

Trans-2-phenethyl-5-phenyl-5,6,11,11a-tetrahydro-1H-imidazo[1',5':1,6]pyrido[3,4-b]indole-1,3(2H)-dione;

Trans-5-phenyl-2-(2-pyridylmethyl)-5,6,11,11a-tetrahydro-1H-imidazo[1',5':1,6]pyrido[3,4-b]indole-1,3(2H)-dione;

Trans-5-phenyl-2-(4-pyridylmethyl)-5,6,11,11a-tetrahydro-1H-imidazo[1',5':1,6]pyrido[3,4-b]indole-1,3(2H)-dione;

Trans-5-(4-methoxyphenyl)-2-(3-pyridylmethyl)-5,6,11,11a-tetrahydro-1H-imidazo[1',5':1,6]pyrido[3,4-b]indole-1,3(2H)-dione;

Trans-2-(2-dimethylaminoethyl)-5-(4-methoxyphenyl)-5,6,11,11a-tetrahydro-1H-imidazo[1',5':1,6]pyrido[3,4-b]indole-1,3(2H)-dione;

Trans-2-(3-dimethylaminopropyl)-5-(4-methoxyphenyl)-5,6,11,11a-tetrahydro-1H-imidazo[1',5':1,6]pyrido[3,4-b]indole-1,3(2H)-dione;

Trans-2-(2-morpholin-4-yl-ethyl)-5-phenyl-5,6,11,11a-tetrahydro-1H-imidazo[1',5':1,6]pyrido[3,4-b]indole-1,3(2H)-dione;

Trans-5-(4-methoxyphenyl)-2-[3-(4-methyl-piperazin-1-yl)-propyl]-5,6,11,11a-tetrahydro-1H-imidazo[1',5':1,6]pyrido[3,4-b]indole-1,3(2H)-dione;

Trans-5-(4-methoxyphenyl)-2-(2-pyrrolidin-1-yl-ethyl)-5,6,11,11a-tetrahydro-1H-imidazo[1',5':1,6]pyrido[3,4-b]indole-1,3(2H)-dione;

Trans-5-(4-methoxyphenyl)-2-[2-(1-methyl-pyrrolidin-2-yl)-ethyl]-5,6,11,11a-tetrahydro-1H-imidazo-[1',5':1,6]pyrido[3,4-b]indole-1,3(2H)-dione;

Trans-5-(4-methoxyphenyl)-5,6,11,11a-tetrahydro-1H-imidazo[1',5':1,6]pyrido[3,4-b]indole-1,3(2H)-dione;
Cis-5-(4-methoxyphenyl)-5,6,11,11a-tetrahydro-1H-imidazo[1',5':1,6]pyrido[3,4-b]indole-1,3(2H)-dione;
and pharmaceutically acceptable salts and solvates thereof.

Particularly preferred compounds of the invention are:
(5R,11aR)-2-benzyl-5-(3,4-methylenedioxyphenyl)-5,6,11,11a-tetrahydro-1H-imidazo[1',5':1,6]pyrido[3,4-b]indole-1,3(2H)-dione;
Cis-2-cyclohexyl-5-(4-methoxyphenyl)-5,6,11,11a-tetrahydro-1H-imidazo[1',5':1,6]pyrido[3,4-b]indole-1,3(2H)-dione;
Trans-2-butyl-5-(4-methoxyphenyl)-5,6,11,11a-tetrohydro-1H-imidazo[1',5':1,6]pyrido[3,4-b]indole-1,3(2H)-dione;
Cis-2-benzyl-5-(3,4-methylenedioxyphenyl)-5,6,11,11a-tetrahydro-1H-imidazo[1',5':1,6]pyrido[3,4-b]indole-1,3(2H)-dione;
and pharmaceutically acceptable salts and solvates thereof.

DETAILED DESCRIPTION OF THE PREFERRED EMBODIMENTS

It has been shown that compounds of the present invention are potent and selective inhibitors of cGMP-specific PDEs 1, 5, and 6, and particularly PDE5. Thus, compounds of formula (I) are of interest for use in therapy, specifically for the treatment of a variety of conditions where inhibition of cGMP-specific PDE is thought to be beneficial.

In summary, the biochemical, physiological, and clinical effects of PDE5 inhibitors suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, male and female erectile dysfunction, and diseases characterized by disorders of gut motility (e.g., irritable bowel syndrome or IBS).

An especially important use is the treatment of male erectile dysfunction, which is one form of impotence and is a common medical problem. Impotence can be defined as a lack of power, in the male, to copulate and can involve an inability to achieve penile erection or ejaculation, or both. The incidence of erectile dysfunction increases with age, with about 50% of men over the age of 40 suffering from some degree of erectile dysfunction.

Many compounds have been investigated for their therapeutic potential in the treatment of MED, including phenoxybenzamine, papaverine, prostaglandin E1 (PGE1), and phentolamine. These compounds, either alone or in combination, are typically self-administered by intracavernosal (i.c.) injection. While such treatments are effective, a treatment that is less invasive than injection therapy is preferred because pain, priapism, and fibrosis of the penis are associated with the i.c. administration of these agents.

For example, alprostadil (i.e., prostaglandin E1) delivered by intraurethral deposition has been approved for the treatment of MED. However, clinical studies showed that this route of administration is not effective in all patients. In addition, phentolamine and apomorphine are being evaluated as oral and sublingual therapies for MED, but neither compound has demonstrated efficacy across a broad range of subjects. Potassium channel openers (KCO) and vasoactive intestinal polypeptide (VIP) also have been shown to be active i.c., but cost and stability issues could limit development of the latter. An alternative to the i.c. route is the use of glyceryl trinitrate (GTN) patches applied to the penis, which has been shown to be effective but produces side effects in both patient and partner.

As an alternative to pharmacological treatment, a variety of penile prostheses have been used to assist achievement of an erection. The short-term success rate is good, but problems with infection and ischemia, especially in diabetic men, make this type of treatment a final option rather than a first-line therapy.

Because of the disadvantages of prior treatments for MED, new strategies to improve erectile response that exploit different physiological mechanisms are being investigated. One area of investigation is increasing the intracellular concentration of cGMP by providing a new type of oral therapy for the treatment of MED.

Increasing cGMP concentration is an important step in the physiology of penile erections. A penile erection is caused by neural stimuli that ultimately cause vasodilation of the arteries and sinusoidal spaces of the corpus cavernosum. Research indicates that nitric oxide plays a central role in this vasodilation.

In particular, atrial natriuretic peptides (ANP) and nitric oxide (NO, sometimes referred to as endothelium-derived relaxing factor or EDRF) relax smooth muscle by increasing guanylyl cyclase activity, which raises intracellular cGMP concentration. Intracellular cGMP is hydrolyzed by phosphodiesterases (PDEs), thereby terminating the action of the cyclic nucleotide. PDE5 is the major cGMP hydrolyzing enzyme in vascular smooth muscle. Accordingly, PDE5 inhibition potentiates the relaxant effects of ANP and nitric oxide by increasing the cGMP levels. Therefore, a compound that inhibits the PDE5 enzyme (and thereby indirectly inhibits the hydrolysis of cGMP) should potentiate the vascular response to nitric oxide, thereby facilitating the achievement and maintenance of erection.

PDE5 inhibitors have potential for use in treating male erectile dysfunction (MED), hypertension, heart failure, and other disease states because of their ability to facilitate the action of ANP and NO. For example, sildenafil, a PDE inhibitor showing little selectivity with respect to PDE6, has the structure:

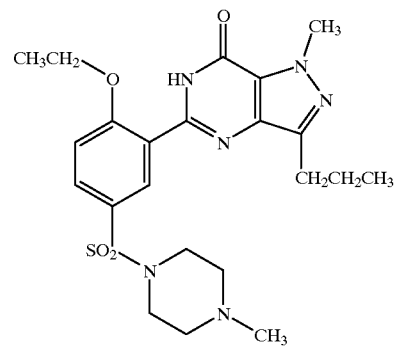

and has shown efficacy in oral administration clinical trials for MED, which supports the hypothesis that augmenting normal or subnormal guanylyl cyclase stimuli has therapeutic benefits.

It is envisioned, therefore, that compounds of formula (I) are useful in the treatment of erectile dysfunction. Furthermore, the compounds can be administered orally, thereby obviating the disadvantages associated with intracavernosal administration. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal, including man.

It also has been observed that human corpus cavernosum contains three distinct PDE enzymes (see A. Taher et al., *J. Urol.*, 149, p. 285A (1993)), one of which is the cGMP-specific PDE5. As a consequence of the selective PDE5 inhibition exhibited by compounds of the present invention, the present compounds sustain cGMP levels, which in turn mediate relaxation of the corpus cavernosum tissue and consequent penile erection.

Although the compounds of the invention are envisioned primarily for the treatment of erectile dysfunction in humans, such as male erectile dysfunction and female sexual dysfunction, including orgasmic dysfunction related to clitoral disturbances, they also can be used for the treatment of premature labor and dysmenorrhea.

It is understood that references herein to treatment extend to prophylaxis, as well as treatment of established conditions.

It also is understood that "a compound of formula (I)," or a physiologically acceptable salt or solvate thereof, can be administered as the neat compound, or as a pharmaceutical composition containing either entity.

A further aspect of the present invention is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™. Oral administration generally is preferred.

With respect to treating sexual dysfunction and particularly erectile dysfunction in humans, oral administration of the compounds of the invention is the preferred route. Oral administration is the most convenient and avoids the disadvantages associated with intracavernosal administration. For patients suffering from a swallowing disorder or from impairment of drug absorption after oral administration, the drug can be administered parenterally, e.g., sublingually or buccally.

For administration to man in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. For example, the compound can be administered orally, buccally, or sublingually in the form of tablets containing excipients such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents (e.g., methylcellulose, a semisynthetic glyceride such as witepsol, or mixtures of glycerides such as a mixture of apricot kernel oil and PEG-6 esters, or mixtures of PEG-8 and caprylic/capric glycerides). A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor.

There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, including man, comprising a compound of formula (I) or a pharmaceutically acceptable salt thereof, together with a pharmaceutically acceptable diluent or carrier.

A compound of formula (I) also can be used in combination with other therapeutic agents which can be useful in the treatment of the above-mentioned and other disease states. The invention thus provides, in another aspect, a combination of a compound of formula (I), together with a second therapeutically active agent.

A compound of formula (I) can be used in the preparation of a medicament for co-administration with the second therapeutically active agent in treatment of conditions where inhibition of a cGMP-specific PDE is beneficial. In addition, a compound of formula (I) can be used in the preparation of a medicament for use as adjunctive therapy with a second therapeutically active compound to treat such conditions. Appropriate doses of known second therapeutic agents for use in combination with a compound of formula (I) are readily appreciated by those skilled in the art.

In particular, because compounds of the present invention maintain cGMP levels, the compounds of formula (I) can provide beneficial antiplatelet, antineutrophil, antivasospastic, vasodilatory, natriuretic, and diuretic activities, as well as potentiate the effects of endothelium-derived relaxing factor (EDRF), gastric NO administration, nitrovasodilators, atrial natriuretic factor (ANF), brain natriuretic peptide (BNP), C-type natriuretic peptide (CNP), and endothelium-dependent relaxing agents such as bradykinin, acetylcholine, and 5-HT$_1$.

The present selective PDE5 inhibitors in combination with vasodilators, including nitric oxide and nitric oxide donators and precursors, such as the organic nitrate vasodilators which act by releasing nitric oxide in vivo, are especially useful in treatment of angina, congestive heart failure, and malignant hypertension (e.g., pheochromocytoma). Related to the capacity of the present PDE5 inhibitors to potentiate nitric oxide donors and precursors is their ability, in spontaneously hypertensive rats, to reverse the desensitization to these agents that occurs with chronic use.

Examples of vasodilators that can be used in conjunction with the compounds of formula (I) include, but are not limited to, (a) organic nitrates, such as nitroglycerin, isosorbide dinitrate, pentaerythrityl tetranitrate, isosorbide-5-mononitrate, propatyl nitrate, trolnitrate, nicroandil, mannitol hexanitrate, inositol hexanitrate, N-[3-nitratopivaloyl]-L-cysteine ethyl ester, (b) organic nitrites, like isoamyl nitrite, (c) thionitrites, (d) thionitrates, (e) S-nitrosothiols, like S-nitroso-N-acetyl-D,L-penicillamine, (f) nitrosoproteins, (g) substituted furoxanes, such as 1,2,5-oxadiazole-2-oxide and furazan-N-oxide, (h) substituted sydnonimines, such as molsidomine and mesocarb, (i) nitrosyl complex compounds, like iron nitrosyl compounds, especially sodium nitroprusside, and (j) nitric oxide (NO) itself.

Other classes of therapeutic agents that can be used in conjunction with the compounds of formula (I), in addition to vasodilators, include, but are not limited to, α-adrenergic blockers, mixed α,β-blockers, prostaglandin EI (PGEI) and prostacyclin (PGI2), angiotensin converting enzyme inhibitors (ACE inhibitors), neutral endopeptidase (NEP) inhibitors, centrally acting dopaminergic agents (such as apomorphine), vasoactive intestinal peptides (VIP), calcium channel blockers, and compounds like thiazides.

Alpha-adrenergic blockers inhibit vasoconstriction in the corpus cavernosum. Because PDE5 inhibitors enhance vasodilation of the same smooth muscle tissue, a PDE5 inhibitor of formula (I) and an α-adrenergic blocker, like phentolamine or prazocin, or a centrally acting dopaminergic agent, like apomorphine, can be expected to potentiate one another in a treatment for MED or other disorders. Potentiation of mixed α,β-blockers, like carvedilol, which is employed in treatment of hypertension, also is expected. Similarly, α$_2$-adrenergic blockers, like yohimbine, can be potentiated.

Prostaglandin E1 enhances relaxation of the corpus cavernosum by increasing the formation of cyclic AMP. Cyclic AMP can be degraded in the corpus cavernosum by PDE3, which is inhibited by cyclic GMP. By maintaining cyclic GMP levels, a PDE5 inhibitor can indirectly inhibit PDE3 activity, and hence block degradation of cyclic AMP. Therefore, a PDE5 inhibitor of formula (I) can be expected to potentiate the activity of PGE1 in the treatment of MED or compounds having similar activities, such as PGI2, in the treatment of pulmonary hypertension, for example.

Angiotensin converting enzyme (ACE) inhibitors block the conversion of angiotensin I into angiotensin II, which causes systemic vasoconstriction and the retention of sodium and water. PDE5 inhibitors cause vasodilation in hypertensive animals, and stimulate the excretion of sodium and water in normotensive animals. Therefore, a PDE5 inhibitor of formula (I) can be combined with an ACE inhibitor to achieve more powerful vasodilatory and natriuretic effects in, for example, treatment of congestive heart failure or hypertensive states.

Neutral endopeptidase (NEP) inhibitors inhibit the degradation of atrial natriuretic peptide (ANP) by NEP. PDE5 inhibitors can be expected to potentiate the action of ANP by inhibiting degradation of its second messenger, cyclic GMP, and, therefore, a compound of formula (I) can potentiate the effects of agents, like NEP inhibitors, that increase blood levels of ANP.

The combination referred to above can be presented for use in the form of a single pharmaceutical formulation, and, thus, pharmaceutical compositions comprising a combination as defined above together with a pharmaceutically acceptable diluent or carrier comprise a further aspect of the invention.

The individual components of such a combination, therefore, can be administered either sequentially or simultaneously from the same or separate pharmaceutical formulations. As is the case for the PDE5 inhibitors of formula (I), a second therapeutic agent can be administered by any suitable route, for example, by oral, buccal, inhalation, sublingual, rectal, vaginal, transurethral, nasal, topical, percutaneous (i.e., transdermal), or parenteral (including intravenous, intramuscular, subcutaneous, and intracoronary) administration.

In some embodiments, the compound of formula (I) and the second therapeutic agent are administered by the same route, either from the same or from different pharmaceutical compositions. However, in other embodiments, using the same route of administration for the compound of formula (I) and the second therapeutic agent either is impossible or is not preferred. For example, if the second therapeutic agent is nitric oxide, which typically is administered by inhalation, the compound of formula (I) must be administered by a different route. Furthermore, if a compound of formula (I) is used in combination with a nitrate vasodilator, for example, in treatment of an erectile dysfunction, it is preferred that the compound of formula (I) is administered orally and the vasodilator is administered topically, and preferably in a manner which avoids substantial systemic delivery of the nitrate.

The combination of a compound of formula (I) and a second therapeutic agent is envisioned in the treatment of several disease states. Examples of such treatments are the systemic and topical treatment of male and female sexual dysfunction, wherein a compound of formula (I) is used in combination with phentolamine, prazocin, apomorphine, PDE1, or a vasoactive intestinal peptide. The compound of formula (I) can be administered orally or transuretherally, and the second therapeutic agent can be administered orally, topically, or intracavernosally, for example. Persons skilled in the art are aware of the best modes of administration for each therapeutic agent, either alone or in a combination.

Other disease states that can be treated by a combination of a compound of formula (I) and a second therapeutic agent include, but are not limited to:

(a) treatment of hypertension using a compound of formula (I) in combination with an α-adrenergic blocker, a mixed α,β-blocker, like carvedilol, a thiazide, sodium nitroprusside, an ACE inhibitor, or a calcium channel blocker;

(b) treatment of pulmonary hypertension using a compound of formula (I) in combination with inhaled NO on other inhaled vasodilators, or with PGI2 administered via an IV pump; and (c) treatment of chronic obstructive pulmonary disease using a compound of formula (I) in combination with inhaled NO.

Compounds of formula (I) can be prepared by any suitable method known in the art or by the following processes which form part of the present invention. In the methods below $R^0$, $R^1$, and $R^2$ are as defined in formula (I) above unless otherwise indicated.

Thus, a process (A) for preparing a compound of formula (I) comprises reacting a compound of formula (II)

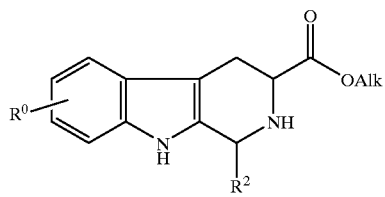

(II)

with an isocyanate of formula $R^1$—N=C=O, in the presence of a suitable organic solvent, such as a ketone solvent, e.g., butanone, acetone, or the like, and under reflux for several hours, e.g., 14 to 16 hours. Alk as used herein represents a $C_{1-6}$alkyl group, e.g., methyl.

Compounds of formula (I) can be prepared as individual enantiomers in two steps from the appropriate enantiomer of formula (III) or as mixtures (e.g., racemates) of either pairs of cis or trans isomers from the corresponding mixtures of either pairs of cis or trans isomers of formula (III).

Individual enantiomers of the compounds of the invention can be prepared from racemates by resolution using methods known in the art for the separation of racemic mixtures into their constituent enantiomers, for example using HPLC (high performance liquid chromatography) on a chiral column such as Hypersil naphthylurea.

A compound of formula (II) can be prepared from a tryptophan derivative, such as an alkyl ester thereof of formula (III)

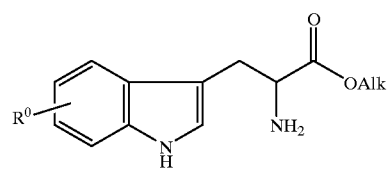

(III)

(where Alk is as previously defined) or a salt thereof (e.g., the hydrochloride salt) according to either of the following procedures (a) and (b). Procedure (b) is only suitable for preparing cis isomers of formula (III) and can be particularly suitable for preparing individual cis enantiomers of formula (III) from D- or L-tryptophan alkyl esters as appropriate.

Procedure (a)

This comprises a Pictet-Spengler cyclization between a compound of formula (III) and an aldehyde $R^2$CHO. The reaction can be conveniently effected in a suitable solvent such as a halogenated hydrocarbon (e.g., dichloromethane) or an aromatic hydrocarbon (e.g., toluene) in the presence of an acid such as trifluoroacetic acid. The reaction can be conveniently carried out at a temperature of from −20° C. to reflux to provide a compound of formula (II) in one step. The reaction also can be carried out in a solvent such as an aromatic hydrocarbon (e.g., benzene or toluene) under reflux, optionally using a Dean-Stark apparatus to trap the water produced.

The reaction provides a mixture of cis and trans isomers which can be either individual enantiomers or racemates of pairs of cis or trans isomers depending upon whether racemic or enantiomerically pure tryptophan alkyl ester was used as the starting material. Individual cis or trans enantiomers can be conveniently separated from mixtures thereof by fractional crystallization or by chromatography (e.g., flash column chromatography) using appropriate solvents and eluents. Similarly, pairs of cis and trans isomers can be separated by chromatography (e.g., flash column chromatography) using appropriate eluents. An optically pure trans isomer also can be converted to an optically pure cis isomer using suitable epimerization procedures. One such procedure comprises treating the trans isomer or a mixture (e.g., 1:1 mixture) of cis and trans isomers with methanolic or aqueous hydrogen chloride at a temperature of from 0° C. to the refluxing temperature of the solution. The mixture then can be subjected to chromatography (e.g., flash column chromatography) to separate the resulting diastereoisomers, or in the procedure utilizing aqueous hydrogen chloride the desired cis isomer precipitates out as the hydrochloride salt which then can be isolated by filtration.

Procedure (b)

This comprises a four-step procedure from a compound of formula (III) or a salt thereof (e.g., the hydrochloride salt). The procedure is particularly suitable for preparing a 1R, 3R isomer of formula (III) from a D-tryptophan alkyl ester of formula (IV) or a salt thereof (e.g., the hydrochloride salt). Thus, a first step (i) comprises treating a compound of formula (IV) with an acid halide $R^2$COHal (where Hal is as previously defined) in the presence of a base, e.g., an organic base such as a trialkylamine (for example, triethylamine), to provide a compound of formula (IV)

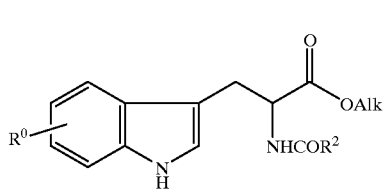

(IV)

The reaction can be conveniently carried out in a suitable solvent such as a halogenated hydrocarbon (e.g., dichloromethane) or an ether (e.g., tetrahydrofuran) and at a temperature of from −20° C. to +40° C.

Step (ii) comprises treating a compound of formula (IV) with an agent to convert the amide group to a thioamide group. Suitable sulphurating agents are well known in the art. Thus, for example, the reaction can be conveniently effected by treating (IV) with Lawesson's reagent. This reaction can be conveniently carried out in a suitable solvent such as an ether (e.g., dimethoxyethane) or an aromatic hydrocarbon (e.g., toluene) at an elevated temperature such as from 40° C. to 80° C. to provide a compound of formula (V)

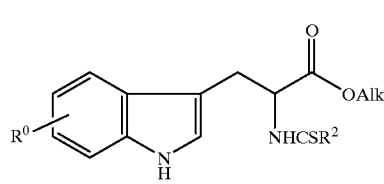

(V)

Step (iii) comprises treating a compound of formula (V) with a suitable agent to provide a compound of formula (VI)

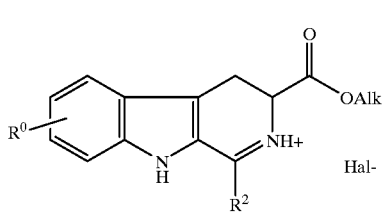

(VI)

(where Hal is a halogen atom, e.g., iodine). The reaction can be conveniently effected by treating (VI) with an alkylating agent such as a methyl halide (e.g., methyl iodide) or an acylating agent such as an acetyl halide (e.g., acetyl chloride) in a suitable solvent such as a halogenated hydrocarbon (e.g., dichloromethane) at an elevated temperature (e.g., under reflux).

In step (iv) the resulting iminium halide of formula (VI) can be treated with a reducing agent such as boron hydride, e.g., sodium borohydride, to provide the desired compound of formula (II). The reduction can be conveniently effected at a low temperature, e.g., within the range of −100° C. to 0° C., in a suitable solvent such as an alcohol (e.g., methanol).

According to a second process (B), a compound of formula (I) can be prepared by reaction of a compound of formula (VII)

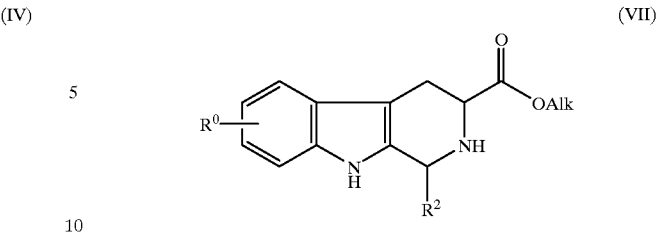

(VII)

where Alk is as previously defined, with the imidazolide of $R^1$—$NH_2$ under suitable conditions. Compounds of formula (VII) are known in the art and can be made by standard methods.

According to a third process (C), a compound of formula (1) where $R^1$ represents hydrogen can be prepared by reacting a compound of formula (VII) with urea at elevated temperature.

The pharmaceutically acceptable acid addition salts of the compounds of formula (I) which contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques.

Compounds of the invention can be isolated in association with solvent molecules by crystallization from or evaporation of an appropriate solvent.

Thus, according to a further aspect of the invention, we provide a process (D) for preparing a compound of formula (I) or a salt or solvate (e.g., hydrate) thereof which comprises process (A) as hereinbefore described followed by i) an interconversion step, and/or either ii) salt formation, or ii) solvate (e.g., hydrate) formation.

The synthesis of the compounds of the invention and of the intermediates for use therein are illustrated by the following, nonlimiting Examples. The following abbreviations are used hereafter in the accompanying examples: rt (room temperature), min (minute), g (gram), mmol (millimole), m.p. (melting point), eq (equivalents), mL (milliliter), μL (microliters), $NaHCO_3$ (sodium bicarbonate), $Na_2SO_4$ (sodium sulfate), MeOH (methyl alcohol), $H_2SO_4$ (sulfuric acid), $N_2$ (nitrogen), and $NH_4OH$ (ammonium hydroxide), $CH_2Cl_2$ (dichloromethane).

Intermediates 1 and 2

Methyl 1,2,3,4-tetrahydro-1-(3,4-methylenedioxyphenyl)-9H-pyrido[3,4-b]indole-3-carboxylate, cis and trans isomers To a stirred solution of racemic tryptophan methyl ester (13 g) and piperonal (9.7 g) in anhydrous $CH_2Cl_2$ (300 mL) cooled at 0° C. was added dropwise trifluoroacetic acid (9 mL) and the solution was allowed to react at ambient temperature. After four days, the yellow solution was diluted with $CH_2Cl_2$ (100 mL), washed with a saturated aqueous solution of $NaHCO_3$, then with water and dried over $Na_2SO_4$. The organic layer was evaporated to dryness under reduced pressure and the residue was purified by flash chromatography eluting with $CH_2Cl_2$/MeOH (99/1) to give first Intermediate 1, the cis isomer (6.5 g) m.p.: 90–93° C., followed by Intermediate 2, the trans isomer (6.4 g) m.p.: 170° C.

The following compounds were obtained in a similar manner:

Intermediates 3 and 4
Methyl 1,2,3,4-tetrahydro-1-(4-methoxyphenyl)-9H-pyrido[3,4-b]indole-3-carboxylate, cis and trans isomers The same method as employed in the preparation of Intermediates 1 and 2 but starting from racemic tryptophan methyl ester and 4-methoxybenzaldehyde gave Intermediate 3, the cis isomer as white crystals m.p.: 142° C., and Intermediate 4, the trans isomer as white crystals m.p.: 209–210° C.

Intermediates 5 and 6
Methyl 1,2,3,4-tetrahydro-1-(2-thienyl)-9H-pyrido[3,4-b]indole-3-carboxylate, cis and trans isomers The same method as employed in the preparation of Intermediates 1 and 2 but starting from racemic tryptophan methyl ester and 2-thiophenecarboxaldehyde gave Intermediate 5, the cis isomer as a pale yellow solid m.p.: 134–137° C., and Intermediate 6, the trans isomer as white crystals m.p.: 169° C.

Intermediate 7
Ethyl 1,2,3,4-tetrahydro-1-(4-dimethylaminophenyl)-9H-pyrido[3,4-b]indole-3-carboxylate, mixture of cis and trans isomers The same method as employed in the preparation of Intermediates 1 and 2 but starting from racemic tryptophan ethyl ester and 4-dimethylaminobenzaldehyde gave the title compound as white crystals m.p.: 170° C.

Intermediates 8 and 9
Methyl 1,2,3,4-tetrahydro-6-fluoro-1-(4-methoxyphenyl)-9H-pyrido[3,4-b]indole-3-carboxylate, cis and trans isomers The same method as employed in the preparation of Intermediates 1 and 2 but starting from racemic 5-fluoro-tryptophan methyl ester and 4-methoxybenzaldehyde gave Intermediate 8, the cis isomer as a solid 1H NMR (CDCl$_3$) δ (ppm) 7.4–6.8 (m, 8H), 5.15 (brs, 1H), 3.9 (dd, 1H), 3.8 (s, 3H), 3.2–2.9 (m, 2H), and Intermediate 9 the trans isomer as a solid m.p.: 197° C.

Intermediates 10 and 11
Methyl 1,2,3,4-tetrahydro-1-(4-chlorophenyl)-9H-pyrido[3,4-b]indole-3-carboxylate, cis and trans isomers The same method as employed in the preparation of Intermediates 1 and 2, but starting from racemic tryptophan methyl ester and 4-chlorobenzaldehyde gave Intermediate 10, the cis isomer as white crystals m.p.: 208–209° C., and Intermediate 11, the trans isomer as white crystals m.p.: 108–109° C.

Intermediates 12 and 13
Methyl 1,2,3,4-tetrahydro-1-(4-trifluoromethylphenyl)-9H-pyrido[3,4-b]indole-3-carboxylate, cis and trans isomers The same method but starting from racemic tryptophan methyl ester and 4-trifluoromethylbenzaldehyde gave Intermediate 12, the cis isomer as pale yellow crystals m.p.: 190° C., and Intermediate 13, the trans isomer as pale yellow crystals m.p.: 203° C.

Intermediates 14 and 15
Ethyl 1,2,3,4-tetrahydro-1-(4-cyanophenyl)-9H-pyrido[3,4-b]indole-3-carboxylate, cis and trans isomers The same method but starting from racemic tryptophan ethyl ester and 4-cyanobenzaldehyde gave Intermediate 14, the cis isomer as white crystals m.p.: 200° C., and Intermediate 15, the trans isomer as white crystals m.p.: 156° C.

Intermediates 16 and 17
Ethyl 1,2,3,4-tetrahydro-1-(4-nitrophenyl)-9H-pyrido[3,4-b]indole-3-carboxylate, cis and trans isomers The same method but starting from racemic tryptophan ethyl ester and 4-nitrobenzaldehyde gave Intermediate 16, the cis isomer as yellow crystals m.p.: 168° C., and Intermediate 17, the trans isomer as yellow crystals m.p.: 195° C.

Intermediates 18 and 19
Ethyl 1,2,3,4-tetrahydro-1-(3-pyridyl)-9H-pyrido-[3,4-b]indole-3-carboxylate, cis and trans isomers The same method but starting from racemic tryptophan ethyl ester and 3-pyridinecarboxaldehyde gave Intermediate 18, the cis isomer as pale yellow crystals m.p.: 230–232° C., and Intermediate 19 the trans isomer as white crystals m.p.: 210–214° C.

Intermediates 20 and 21
Ethyl 1,2,3,4-tetrahydro-1-(3-thienyl)-9H-pyrido-[3,4-b]indole-3-carboxylate, cis and trans isomers The same method as employed in the preparation of Intermediates 1 and 2 but starting from racemic tryptophan ethyl ester and 3-thiophenecarboxaldehyde gave Intermediate 20 the cis isomer as white crystals m.p.: 130° C., and Intermediate 21 the trans isomer as white crystals m.p.: 182–184° C.

Intermediate 22
Methyl 1,2,3,4-tetrahydro-1-(3-furyl)-9H-pyrido[3,4-b]indole-3-carboxylate, mixture of cis and trans isomers The same method but starting from racemic tryptophan methyl ester and 3-furaldehyde gave the title compound as a yellow solid m.p.: 130° C.

Intermediates 23 and 24
(1R,3R)-Methyl 1,2,3,4-tetrahydro-1-(3,4-methylenedioxyphenyl)-9H-pyrido[3,4-b]indole-3-carboxylate, cis isomer and
(1S,3R)-methyl 1,2,3,4-tetrahydro-1-(3,4-methylenedioxyphenyl)-9H-pyrido[3,4-b]indole-3-carboxylate trans isomer To a stirred solution of D-tryptophan methyl ester (11 g) and piperonal (7.9 g) in anhydrous CH$_2$Cl$_2$ (400 mL) cooled at 0° C. was added dropwise trifluoroacetic acid (7.7 mL) and the solution was allowed to react at ambient temperature. After 4 days, the yellow solution was diluted with CH$_2$Cl$_2$ (200 mL) and washed with a saturated aqueous solution of NaHCO$_3$, then with water (3×200 mL) and dried over Na$_2$SO$_4$. The organic layer was evaporated under reduced pressure and the residue was purified by flash chromatography eluting with dichloromethane/ethyl acetate (97/3) to give first Intermediate 23 the cis isomer (6.5 g) m.p.: 154° C. followed by Intermediate 24 the trans isomer (8.4 g) m.p.: 188° C.

Intermediate 25
Ethyl 1,2,3,4-tetrahydro-6-methyl-1-phenyl-9H-pyrido[3,4-b]indole-3-carboxylate, cis and trans isomers To a stirred mixture of racemic 5-methyltryptophan (4 g) in 1N H$_2$SO$_4$ (18 mL) and water (54 mL) was added benzaldehyde (2 mL) and the solution was heated at 80° C. under N$_2$ for 48 hours. The precipitated product was collected by filtration, washed with water and dried. The crude acid (4.5 g) was then dissolved in ethanol (100 mL) and the solution was cooled at −10° C. Thionyl chloride (1.2 mL) was added dropwise to the solution and the mixture was heated at 60° C. for 48 hours. The solvent was removed under reduced pressure and the residue was taken up in ice water and basified with NH$_4$OH. The precipitated compound was washed with water, dried and purified by flash chromatography eluting with dichloromethane/methanol (98/2) to give first the cis isomer (1.7 g) m.p.: 128–130° C., followed by the trans isomer (0.53 g) m.p.: 198–200° C.

Intermediate 26
Ethyl 1,2,3,4-tetrahydro-6-bromo-1-phenyl-9H-pyrido[3,4-b]indole-3-carboxylate, cis and trans isomers The same procedure as described in the preparation of Intermediate 25 but starting from racemic 5-bromo-tryptophan and benzaldehyde gave the cis isomer as white crystals m.p.: 157–160° C. and the trans isomer as white crystals m.p.: 212–216° C.

Intermediate 27

Methyl 1,2,3,4-tetrahydro-1-(3-chlorophenyl)-9H-pyrido[3,4-b]indole-3-carboxylate, mixture of cis and trans isomers The same method as employed in the preparation of Intermediate 1 and 2 but starting from racemic tryptophan methyl ester and 3-chlorobenzaldehyde gave the title compound as white solid m.p.: 150–160° C.

Intermediate 28

Methyl 1,2,3,4-tetrahydro-1-(4-fluorophenyl)-9H-pyrido[3,4-b]indole-3-carboxylate, cis and trans isomers The same method as employed in the preparation of Intermediate 1 and 2 but starting from racemic tryptophan methyl ester and 4-fluorobenzaldehyde gave the cis isomer as white crystals m.p.: 92° C., and the trans isomer as pale yellow crystals m.p.: 183° C.

Intermediate 29

Methyl 1,2,3,4-tetrahydro-1-(4-hydroxyphenyl)-9H-pyrido[3,4-b]indole-3-carboxylate, trans isomer To a stirred solution of racemic tryptophan methyl ester (3 g) and 4-hydroxybenzaldehyde (1.84 g) in anhydrous dichloromethane (50 mL) cooled at 0° C. was added dropwise trifluoroacetic acid (1.27 mL) and the solution was allowed to react at ambient temperature. After 22 hours, the solution was washed with a saturated solution of $NaHCO_3$, then with water, dried over $Na_2SO_4$ and evaporated to dryness. The residue was purified by flash chromatography eluting with ethyl acetate to give the title compound (3.48 g) as an off-white solid m.p.: 233–235° C.

Example 1

Cis-2-benzyl-5-(3,4-methylenedioxyphenyl)-5,6,11,11a-tetrahydro-1H-imidazo [1',5':1,6]pyrido-[3,4-b]indole-1,3(2H)-dione and Trans-2-benzyl-5-(3,4-methylenedioxyphenyl)-5,6,11,11a-tetrahydro-1H-imidazo [1',5':1,6]pyrido-[3,4-b]indole-1,3(2H)-dione To a stirred solution of a mixture of cis and trans isomers of Intermediates 1 and 2 (1 g, 2.85 mmol) in 2-butanone (50 mL) was added dropwise benzyl isocyanate (0.37 mL, 2.99 mmol) and the mixture was refluxed for 15 hours. The solvent was then removed under reduced pressure and the residue was purified by flash chromatography eluting with toluene/ethyl acetate: 85/15 to give first, the trans isomer (240 mg) as white crystals after recrystallization from diethyl ether. m.p.: 208–210° C.

Analysis for $C_{27}H_{21}N_3O_4$: Calculated: C,71.83; H,4.69; N,9.31; Found: C,71.46; H,4.77; N,9.24%;

and followed by the cis isomer (470 mg) as white crystals after recrystallization from ethanol. m.p.: 159–161° C.

Analysis for $C_{27}H_{21}N_3O_4$: Calculated: C,71.83; H,4.69; N,9.31; Found: C,71.79; H,4.80; N,9.09%.

Example 2

Cis-5-(4-methoxyphenyl)-2-methyl-5,6,11,11a-tetrahydro-1H-imidazo [1',5':1,6]pyrido[3,4-b]indole-1,3(2H)-dione The same method as employed in the preparation of Example 1 but starting from Intermediate 3 and methyl isocyanate gave after recrystallization from ethanol, the title compound as white crystals m.p.: 233–240° C.

Analysis for $C_{21}H_{19}N_3O_3$: Calculated: C,69.79; H,5.30; N,11.63; Found: C,69.63; H,5.29; N,11.68%.

Example 3

Cis-2-ethyl-5-(4-methoxyphenyl)-5,6,11,11a-tetrahydro-1H-imidazo[1',5': 1,6]pyrido[3,4-b]indole-1,3(2H)-dione and Trans-2-ethyl-5-(4-methoxyphenyl)-5,6,11,11a-tetrahydro-1H-imidazo[1',5':1,6]pyrido[3,4-b]indole-1,3(2H)-dione The same method as employed in the preparation of Example 1 but starting from a mixture of Intermediates 3 and 4 and ethyl isocyanate gave the cis isomer as white crystals after recrystallization from ethanol m.p.: 210–220° C.

Analysis for $C_{22}H_{21}N_3O_3$: Calculated: C,70.38; H,5.64; N,11.19; Found: C,69.97; H,5.71; N,10.83%.

and the trans isomer as white crystals after recrystallization from 2-propanol m.p.: 245–248° C. Analysis for $C_{22}H_{21}N_3O_3$: Calculated: C,70.38; H,5.64; N,11.19; Found: C,70.28; H,5.76; N,11.22%.

Example 4

Trans-2-ethyl-5-(3,4-methylenedioxyphenyl)-5,6,11,11a-tetrahydro-1H-imidazo [1',5':1,6]pyrido-[3,4-b]indole-1,3(2H)-dione The same method as employed in the preparation of Example 1 but starting from the Intermediate 2 and ethyl isocyanate gave after recrystallization from ethyl acetate/hexane, the title compound as white crystals m.p.: 238° C.

Analysis for $C_{22}H_{19}N_3O_4$: Calculated: C,67.86; H,4.92; N,10.79; Found: C,68.32; H,4.90; N,10.90%.

Example 5

Trans-2-ethyl-5-(2-thienyl)-5,6,11,11a-tetrahydro-1H-imidazo[1',5':1,6]pyrido[3,4-b]indole-1,3(2H)-dione The same method as employed in the preparation of Example 1 but starting from Intermediate 6 and ethyl isocyanate gave after recrystallization from 2-propanol, the title compound as white crystals m.p.: 242–248° C.

Analysis for $C_{19}H_{17}N_3O_2S$: Calculated: C,64.94; H,4.88; N,11.96; Found: C,64.79; H,5.00; N,11.88%.

Example 6

Trans-5-(4-dimethylaminophenyl)-2-ethyl-5,6,11,11a-tetrahydro-1H-imidazo [1',5':1,6]pyrido[3,4-b]indole-1,3(2H)-dione The same method as employed in the preparation of Example 1 but starting from a mixture of cis and trans isomers of Intermediate 7 and ethyl isocyanate gave after recrystallization from methanol, the title compound as white crystals m.p.: 262–265° C.

Analysis for $C_{23}H_{24}N_4O_2$: Calculated: C,71.11; H,6.23; N,14.42; Found: C,71.01; H,6.29; N,14.49%.

Example 7

Trans-2-butyl-9-methyl-5-phenyl-5,6,11,11a-tetrahydro-1H-imidazo [1',5':1,6]pyrido[3,4-b]indole-1,3(2H)-dione The same method as employed in the preparation of Example 1 but starting from the trans isomer of Intermediate 25 and butyl isocyanate gave after recrystallization from diisopropyl ether, the title compound as white crystals m.p.: 196–198° C.

Analysis for $C_{24}H_{25}N_3O_2$: Calculated: C,74.39; H,6.50; N,10.84; Found: C,74.38; H,6.52; N,10.63%.

Example 8

Trans-9-bromo-2-butyl-5-phenyl-5,6,11,11a-tetrahydro-1H-imidazo [1',5':1,6]pyrido[3,4-b]indole-1,3(2H)-dione The same method as employed in the preparation of Example 1 but starting from the trans isomer of Intermediate 26 and butyl isocyanate gave after recrystallization from diisopropyl ether, the title compound as white crystals m.p.: 207–210° C.

Analysis for $C_{23}H_{22}BrN_3O_2$: Calculated: C,61.07; H,4.90; Br,17.66; N,9.29; Found: C,61.28; H,4.95; Br,17.53; N,9.10%.

Example 9

Cis-2-butyl-5-(4-methoxyphenyl)-5,6,11,11a-tetrahydro-1H-imidazo [1',5':1,6] pyrido[3,4-b]indole-1,3(2H)-dione The same method as employed in the preparation of Example 1 but starting from the Intermediate 3 and butyl isocyanate gave after recrystallization from methanol, the title compound as white crystals m.p.: 220–225° C.

Analysis for $C_{24}H_{25}N_3O_3$: Calculated: C,71.44; H,6.25; N,10.41; Found: C,71.56; H,6.23; N,10.36%.

Example 10

Trans-2-butyl-5-(4-methoxyphenyl)-5,6,11,11a-tetrahydro-1H-imidazo[1',5':1,6]pyrido[3,4-b]indole-1,3(2H)-dione The same method as employed in the preparation of Example 1 but starting from the Intermediate 4 and butyl isocyanate gave after recrystallization from ethanol/water, the title compound as white crystals m.p.: 173–174° C.

Analysis for $C_{24}H_{25}N_3O_3$: Calculated: C,71.44; H,6.25; N,10.41; Found: C,71.53; H,6.20; N,10.28%.

Example 11

Cis-2-butyl-9-fluoro-5-(4-methoxyphenyl)-5,6,11,11a-tetrahydro-1H-imidazo [1',5':1,6]pyrido[3,4-b]indole-1,3 (2H)-dione The same method as employed in the preparation of Example 1 but starting from Intermediate 8 and butyl isocyanate gave after recrystallization from methanol, the title compound as white crystals m.p.: 125–130° C.

Analysis for $C_{24}H_{24}FN_3O_3(0.3H_2O)$ Calculated: C,67.53; H,5.81; N,9.84; Found: C,67.19; H,5.74; N,9.85%.

Example 12

Trans-2-butyl-9-fluoro-5-(4-methoxyphenyl)-5,6,11,11a-tetrahydro-1H-imidazo [1',5':1,6]pyrido-[3,4-b]indole-1,3 (2H)-dione The same method as employed in the preparation of Example 1 but starting from the Intermediate 9 and butyl isocyanate gave after recrystallization from diisopropyl ether/pentane, the title compound as white crystals m.p.: 187–189° C.

Analysis for $C_{24}H_{24}FN_3O_3$: Calculated: C,68.39; H,5.74; N,9.97; Found: C,68.61; H,5.71; N,10.04%.

Example 13

Trans-2-butyl-5-(3,4-methylenedioxyphenyl)-5,6,11,11a-tetrahydro-1H-imidazo[1',5':1,6]pyrido[3,4-b]indole-1,3 (2H)-dione The same method as employed in the preparation of Example 1 but starting from Intermediate 2 and butyl isocyanate gave after recrystallization from 2-propanol, the title compound as white crystals m.p.: 152° C.

Analysis for $C_{24}H_{23}N_3O_4$: Calculated: C,69.05; H,5.55; N,10.07; Found: C,68.93; H,5.49; N,9.99%.

Example 14

Cis-2-butyl-5-(3-chlorophenyl)-5,6,11,11a-tetrahydro-1H-imidazo[1',5':1,6]pyrido[3,4-b]indole-1,3(2H)-dione and Trans-2-butyl-5-(3-chlorophenyl)-5,6,11,11a-tetrahydro-1H-imidazo[1',5':1,6]pyrido[3,4-b]indole-1,3(2H)-dione The same method as employed in the preparation of Example 1 but starting from a mixture of cis and trans isomers of Intermediate 27 and butyl isocyanate gave the cis isomer as pale yellow crystals after recrystallization from diethyl ether/cyclohexane m.p.: 215–217° C.

Analysis for $C_{23}H_{22}ClN_3O_2$: Calculated: C,67.73; H,5.44; Cl,8.69; N,10.30; Found: C,67.62; H,5.49; Cl,8.59; N,10.03%.

and the trans isomer as white crystals after recrystallization from ethanol m.p.: 207–209° C. Analysis for $C_{23}H_{22}ClN_3O_2$: Calculated: C,67.73; H,5.44; Cl,8.69; N,10.30; Found: C,67.60; H,5.41; Cl,8.77; N,10.20%.

Example 15

Cis-2-butyl-5-(4-chlorophenyl)-5,6,11,11a-tetrahydro-1H-imidazo[1',5':1,6]pyrido[3,4-b]indole-1,3(2H)-dione The same method as employed in the preparation of Example 1 but starting from Intermediate 10 and butyl isocyanate gave after recrystallization from methanol, the title compound as pale yellow crystals m.p.: 252° C.

Analysis for $C_{23}H_{22}ClN_3O_2$: Calculated: C,67.73; H,5.44; Cl,8.69; N,10.30; Found: C,67.60; H,5.44; Cl,8.55; N,10.30%.

Example 16

Trans-2-butyl-5-(4-chlorophenyl)-5,6,11,11a-tetrahydro-1H-imidazo[1',5':1,6]pyrido[3,4-b]indole-1,3(2H)-dione The same method as employed in the preparation of Example 1 but starting from Intermediate 11 and butyl isocyanate gave after recrystallization from methanol, the title compound as pale yellow crystals m.p.: 174° C.

Analysis for $C_{23}H_{22}ClN_3O_2$: Calculated: C,67.73; H,5.44; Cl,8.69; N,10.30; Found: C,67.75; H,5.49; Cl,8.75; N,10.46%.

Example 17

Trans-2-butyl-5-(4-fluorophenyl)-5,6,11,11a-tetrahydro-1H-imidazo[1',5':1,6]pyrido[3,4-b]indole-1,3(2H)-dione The same method as employed in the preparation of Example 1 but starting from the trans isomer of Intermediate 28 and butyl isocyanate gave after recrystallization from 2-propanol, the title compound as pale yellow crystals m.p.: 242° C.

Analysis for $C_{23}H_{22}FN_3O_2$: Calculated: C,70.57; H,5.66; F,4.85; N,10.73; Found: C,70.57; H,5.63; F,4.66; N,10.83%.

Example 18

Trans-2-butyl-5-(4-hydroxyphenyl)-5,6,11,11a-tetrahydro-1H-imidazo[1',5':1,6]pyrido[3,4-b]indole-1,3(2H)-dione The same method as employed in the preparation of Example 1 but starting from Intermediate 29 and butyl isocyanate gave after recrystallization from 2-propanol/water, the title compound as white crystals m.p.: 259° C.

Analysis for $C_{23}H_{23}N_3O_3$: Calculated: C,70.93; H,5.95; N,10.79; Found: C,70.41; H,6.04; N,10.63%.

Example 19

Cis-2-butyl-5-(4-trifluoromethylphenyl)-5,6,11,11a-tetrahydro-1H-imidazo[1',5':1,6]pyrido[3,4-b]indole-1,3 (2H)-dione The same method as employed in the preparation of Example 1 but starting from Intermediate 12 and butyl isocyanate gave after recrystallization from methanol/water, the title compound as pale yellow crystals m.p.: 232° C.

Analysis for $C_{24}H_{22}F_3N_3O_2$: Calculated: C,65.30; H,5.02; F,12.91; N,9.52; Found: C,65.29; H,5.05; F,12.56; N,9.37%.

Example 20

Cis-2-butyl-5-(4-cyanophenyl)-5,6,11,11a-tetrahydro-1H-imidazo[1',5':1,6]pyrido[3,4-b]indole-1,3(2H)-dione The same method as used in the preparation of Example 1 but starting from Intermediate 14 and butyl isocyanate gave after recrystallization from 2-propanol, the title compound as white crystals m.p.: 260° C.

Analysis for $C_{24}H_{22}N_4O_2$: Calculated: C,72.34; H,5.57; N,14.06; Found: C,72.30; H,5.59; N,14.08%.

Example 21

Trans-2-butyl-5-(4-cyanophenyl)-5,6,11,11a-tetrahydro-1H-imidazo[1',5':1,6]pyrido[3,4-b]indole-1,3(2H)-dione The same method as employed in the preparation of Example 1 but starting from Intermediate 15 and butyl isocyanate gave after recrystallization from diethyl ether/cyclohexane, the title compound as white crystals m.p.: 158° C.

Analysis for $C_{24}H_{22}N_4O_2$: Calculated: C,72.34; H,5.57; N,14.06; Found: C,72.40; H,5.56; N,13.95%.

Example 22

Cis-2-butyl-5-(4-nitrophenyl)-5,6,11,11a-tetrahydro-1H-imidazo[1',5':1,6]pyrido[3,4-b]indole-1,3(2H)-dione Trans-2-butyl-5-(4-nitrophenyl)-5,6,11,11a-tetrahydro-1H-imidazo[1',5':1,6]pyrido[3,4-b]indole-1,3(2H)-dione The same method as employed in the preparation of Example 1 but starting from a mixture of Intermediates 16 and 17 and butyl isocyanate gave the cis isomer as yellow crystals after recrystallization from methanol m.p.: 236° C.

Analysis for $C_{23}H_{22}N_4O_4$: Calculated: C,66.02; H,5.30; N,13.39; Found: C,65.82; H,5.36; N,13.25%.
and the trans isomer as yellow crystals after recrystallization from 2-propanol m.p.: 206° C.

Analysis for $C_{23}H_{22}N_4O_4$ Calculated: C,66.02; H,5.30; N,13.39; Found: C,66.12; H,5.38; N,13.28%.

Example 23
Cis-2-butyl-5-(3-pyridyl)-5,6,11,11a-tetrahydro-1H-imidazo[1',5':1,6]pyrido[3,4-b]indole-1,3(2H)-dione The same method as employed in the preparation of Example 1 but starting from Intermediate 18 and butyl isocyanate gave after recrystallization from 2-propanol, the title compound as white crystals m.p.: 257–263° C.

Analysis for $C_{22}H_{22}N_4O_2$: Calculated: C,70.57; H,5.92; N,14.96; Found: C,70.38; H,6.07; N,14.88%.

Example 24
Cis-2-butyl-5-(3-thienyl)-5,6,11,11a-tetrahydro-1H-imidazo[1',5':1,6]pyrido[3,4-b]indole-1,3(2H)-dione and
Trans-2-butyl-5-(3-thienyl)-5,6,11,11a-tetrahydro-1H-imidazo[1',5':1,6]pyrido[3,4-b]indole-1,3(2H)-dione The same method as employed in the preparation of Example 1 but starting from a mixture of Intermediates 20 and 21 and butyl isocyanate gave the cis isomer as white crystals after recrystallization from 2-propanol m.p.: 219–221° C.

Analysis for $C_{21}H_{21}N_3O_2S$: Calculated: C,66.47; H,5.58; N,11.07; S,8.45; Found: C,66.13; H,5.68; N,11.00; S,8.27%.
and the trans isomer as white crystals after recrystallization from ethyl acetate m.p.: 240–242° C.

Analysis for $C_{21}H_{21}N_3O_2S$: Calculated: C,66.47; H,5.58; N,11.07; S,8.45; Found: C,66.68; H,5.69; N,11.05; S,8.56%.

Example 25
Cis-2-butyl-5-(3-furyl)-5,6,11,11a-tetrahydro-1H-imidazo[1',5':1,6]pyrido[3,4-b]indole-1,3(2H)-dione and
Trans-2-butyl-5-(3-furyl)-5,6,11,11a-tetrahydro-1H-[1',5':1,6]pyrido[3,4-b]indole-1,3(2H)-dione The same method but starting from a mixture of cis and trans isomers Intermediate 22 and butyl isocyanate gave the cis isomer as white crystals after recrystallization from toluene m.p.: 155–160° C.

Analysis for $C_{21}H_{21}N_3O_3$: Calculated: C,69.41; H,5.82; N,11.56; Found: C,69.44; H,5.86; N,11.52%.
and the trans isomer as pale yellow crystals after recrystallization from ethanol m.p.: 215–219° C.

Analysis for $C_{21}H_{21}N_3O_3$: Calculated: C,69.41; H,5.82; N,11.56; Found: C,69.43; H,5.73; N,11.46%.

Example 26
Cis-2-cyclohexyl-5-(4-methoxyphenyl)-5,6,11,11a-tetrahydro-1H-imidazo[1',5':1,6]pyrido[3,4-b]indole-1,3(2H)-dione and
Trans-2-cyclohexyl-5-(4-methoxyphenyl)-5,6,11,11a-tetrahydro-1H-imidazo[1',5':1,6]pyrido[3,4-b]indole-1,3(2H)-dione The same method as employed in the preparation of Example 1 but starting from a mixture of Intermediates 3 and 4 and cyclohexyl isocyanate gave the cis isomer as white crystals after recrystallization from ethanol m.p.: 250–260° C.

Analysis for $C_{26}H_{27}N_3O_3$: Calculated: C,72.71; H,6.34; N,9.78; Found: C,72.73; H,6.39; N,9.63%.
and the trans isomer as white crystals after recrystallization from 2-propanol m.p.: 265–269° C. Analysis for $C_{26}H_{27}N_3O_3$: Calculated: C,72.71; H,6.34; N,9.78; Found: C,72.82; H,6.38; N,9.69%.

Example 27
Cis-2-cyclohexyl-9-fluoro-5-(4-methoxyphenyl)-5,6,11,11a-tetrahydro-1H-imidazo[1',5':1,6]pyrido[3,4-b]indole-1,3(2H)-dione The same method as employed in the preparation of Example 1 but starting from Intermediate 8 and cyclohexyl isocyanate gave after recrystallization from methanol, the title compound as white crystals m.p.: 275–278° C.

Analysis for $C_{26}H_{26}FN_3O_3$: Calculated: C,69.78; H,5.86; N,9.39; Found: C,69.75; H,5.85; N,8.96%.

Example 28
Trans-2-cyclohexyl-9-fluoro-5-(4-methoxyphenyl)-5,6,11,11a-tetrahydro-1H-imidazo[1',5':1,6]pyrido[3,4-b]indole-1,3(2H)-dione The same method as employed in the preparation of Example 1 but starting from Intermediate 9 and cyclohexyl isocyanate gave after recrystallization from ethanol, the title compound as white crystals m.p.: 265–267° C.

Analysis for $C_{26}H_{26}FN_3O_3$: Calculated: C,69.78; H,5.86; N,9.39; Found: C,69.71; H,5.91; N,9.37%.

Example 29
Trans-2-benzyl-5-phenyl-5,6,11,11a-tetrahydro-1H-imidazo[1',5':1,6]pyrido[3,4-b]indole-1,3(2H)-dione The same method as employed in the preparation of Example 1 but starting from trans methyl 1,2,3,4-tetrahydro-1-phenyl-9H-pyrido[3,4-b]indole-3-carboxylate (see J. Cook et al., *Heterocycles*, 4(7), 1249–1255 (1976)) and benzyl isocyanate gave after recrystallization from diethyl ether, the title compound as white crystals m.p.: 200–202° C.

Analysis for $C_{26}H_{21}N_3O_2$: Calculated: C,76.64; H,5.19; N,10.31; Found: C,76.75; H,5.18; N,10.23%.

Example 30
Cis-2-benzyl-5-(4-methoxyphenyl)-5,6,11,11a-tetrahydro-1H-imidazo[1',5':1,6]pyrido[3,4-b]indole-1,3(2H)-dione The same method as employed in the preparation of Example 1 but starting from Intermediate 3 and benzyl isocyanate gave after recrystallization from ethanol, the title compound as pale yellow crystals m.p.: 240–243° C.

Analysis for $C_{27}H_{23}N_3O_3$: Calculated: C,74.13; H,5.30; N,9.60; Found: C,74.13; H,5.31; N,9.58%.

Example 31
Trans-2-benzyl-5-(4-methoxyphenyl)-5,6,11,11a-tetrahydro-1H-imidazo[1',5':1,6]pyrido[3,4-b]indole-1,3(2H)-dione The same method as employed in the preparation of Example 1 but starting from Intermediate 4 and benzyl isocyanate gave after recrystallization from 2-propanol, the title compound as white crystals m.p.: 208–212° C.

Analysis for $C_{27}H_{23}N_3O_3$: Calculated: C,74.13; H,5.30; N,9.60; Found: C,74.25; H,5.47; N,9.49%.

Example 32
(5R,11aR)-2-benzyl-5-(3,4-methylenedioxyphenyl)-5,6,11,11a-tetrahydro-1H-imidazo-[1',5':1,6]pyrido[3,4-b]indole-1,3(2H)-dione The same method as employed in the preparation of Example 1 but starting from Intermediate 23 and benzyl isocyanate, gave after recrystallization toluene, the title compound as white crystals m.p.: 145° C.

Analysis for $C_{27}H_{21}N_3O_4$: Calculated: C,71.83; H,4.69; N,9.31; Found: C,71.47; H,4.74; N,9.28%.

Example 33
Trans-2-benzyl-5-(4-hydroxyphenyl)-5,6,11,11a-tetrahydro-1H-imidazo[1',5':1,6]pyrido[3,4-b]indole-1,3(2H)-dione The same method as employed in the preparation of Example 1 but starting from Intermediate 29 and benzyl isocyanate gave after recrystallization from methanol, the title compound as white crystals m.p.: 268–272° C. Analysis for $C_{26}H_{21}N_3O_3$: Calculated: C,73.74; H,5.00; N,9.92; Found: C,73.63; H,5.09; N,10.02%.

Example 34

Trans-2-(2-chloroethyl)-5-(4-methoxyphenyl)-5,6,11,11a-tetrahydro-1H-imidazo[1',5':1,6]pyrido[3,4-b]indole-1,3(2H)-dione The same method as employed in the preparation of Example 1 but starting from Intermediate 4 and 2-chloroethyl isocyanate, gave after recrystallization from diethyl ether/hexane, the title compound as white crystals m.p.: 218–219° C.

Analysis for $C_{22}H_{20}ClN_3O_3$: Calculated: C,64.47; H,4.92; Cl,8.65; N,10.25; Found: C,64.44; H,4.98; Cl,8.81; N,10.20%.

Example 35

Cis-2-benzyl-5-cyclohexyl-5,6,11,11a-tetrahydro-1H-imidazo[1',5':1,6]pyrido[3,4-b]indole-1,3(2H)-dione The same method as employed in the preparation of Example 1 but starting from cis methyl 1,2,3,4-tetrahydro-1-cyclohexyl-9H-pyrido[3,4-b]indole-3-carboxylate (see J. Cook et al., *Heterocycles*, 4(7), 1249–1255 (1976)) and benzyl isocyanate gave after recrystallization from methanol, the title compound as white crystals m.p.: 170–173° C.

Analysis for $C_{26}H_{27}N_3O_2$: Calculated: C,75.52; H,6.58; N,10.16; Found: C,75.63; H,6.48; N,9.75%.

Example 36

Trans-2-benzyl-5-cyclohexyl-5,6,11,11a-tetrahydro-1H-imidazo[1',5':1,6]pyrido[3,4-b]indole-1,3(2H)-dione The same method as employed in the preparation of Example 1 but starting from trans methyl 1,2,3,4-tetrahydro-1-cyclohexyl-9H-pyrido[3,4-b]indole-3-carboxylate (see J. Cook et al., *Heterocycles*, 4(7), 1249–1255 (1976)) and benzyl isocyanate gave after recrystallization from methanol, the title compound as white crystals m.p.: 130–135° C.

Analysis for $C_{26}H_{27}N_3O_2$: Calculated: C,75.52; H,6.58; N,10.16; Found: C,75.74; H,6.67; N,9.94%.

Example 37

Trans-2-butyl-5-phenyl-5,6,11,11a-tetrahydro-1H-imidazo[1',5':1,6]pyrido[3,4-b]indole-1,3(2H)-dione The same method as employed in the preparation of Example 1 but starting from trans methyl 1,2,3,4-tetrahydro-1-phenyl-9H-pyrido[3,4-b]indole-3-carboxylate and butyl isocyanate gave after recrystallization from 2-propanol, the title compound as white crystals m.p.: 240–243° C.

Analysis for $C_{23}H_{23}N_3O_2$: Calculated: C,73.97; H,6.21; N,11.25; Found: C,73.95; H,6.32; N,11.28%.

Example 38

Trans-2-cyclohexyl-5-phenyl-5 6,11,11a-tetrahydro-1H-imidazo[1',5':1,6]pyrido[3,4-b]indole-1,3(2H)-dione The same method as employed in the preparation of Example 1 but starting from trans methyl 1,2,3,4-tetrahydro-1-phenyl-9H-pyrido[3,4-b]indole-3-carboxylate and cyclohexyl isocyanate gave after recrystallization from methanol, the title compound as white crystals m.p.: 248–250° C.

Analysis for $C_{25}H_{25}N_3O_2$: Calculated: C,75.16; H,6.31; N,10.52; Found: C,75.23; H,6.33; N,10.60%.

Example 39

Cis-2-cyclohexyl-5-phenyl-5,6,11,11a-tetrahydro-1H-imidazo[1',5':1,6]pyrido[3,4-b]indole-1,3(2H)-dione The same method as employed in the preparation of Example 1 but starting from cis methyl 1,2,3,4-tetrahydro-1-phenyl-9H-pyrido[3,4-b]indole-3-carboxylate and cyclohexyl isocyanate gave after recrystallization from methanol, the title compound as white crystals m.p.: 267–270° C.

Analysis for $C_{25}H_{25}N_3O_2$: Calculated: C,75.16; H,6.31; N,10.52; Found: C,75.20; H,6.33; N,10.52%.

Example 40

Trans-2-ethoxycarbonylmethyl-5-(4-methoxyphenyl)-5,6,11,11a-tetrahydro-1H-imidazo[1',5':1,6]pyrido[3,4-b]indole-1,3(2H)-dione The same method as employed in the preparation of Example 1 but starting from Intermediate 4 and ethyl isocyanatoacetate gave after recrystallization from ethanol, the title compound as white crystals m.p.: 165–167° C.

Analysis for $C_{24}H_{23}N_3O_5$: Calculated: C,66.50; H,5.35; N,9.69; Found: C,66.66; H,5.32; N,9.66%.

Example 41

Trans-5-(4-methoxyphenyl)-2-[2-(2-pyridyl)-ethyl]-5,6,11,11a-tetrahydro-1H-imidazo[1',5':1,6]pyrido[3,4-b]indole-1,3(2H)-dione To a stirred solution of carbonyl diimidazole (0.28 g, 1.72 mmol) in dry tetrahydrofuran (5 mL), was added dropwise a solution of 2-(2-aminoethyl)pyridine (0.205 g, 1.68 mmol) in tetrahydrofuran (3 mL) and the solution was stirred at room temperature for 0.5 hour. Then, a solution of Intermediate 4 (0.5 g, 1.43 mmol) in dry tetrahydrofuran (7 mL) was added and the resulting solution was refluxed for 20 hours. The solvent was removed under reduced pressure and the residue was dissolved in dichloromethane (50 mL). The solution was washed three times with water (3×20 mL), dried over Na2SO4 and concentrated. The residue was then purified by flash chromatography eluting with dichloromethane/methanol: 99/1 and recrystallised from ethanol/water to give the title compound (0.35 g) as white crystals m.p.: 140–143° C.

Analysis for $C_{27}H_{24}N_4O_3$: Calculated: C,71.67; H,5.35; N,12.38; Found: C,71.87; H,5.41; N,12.28%.

Example 42

Trans-2-cyclopropyl-5-phenyl-5,6,11,11a-tetrahydro-1H-imidazo[1',5':1,6]pyrido[3,4-b]indole-1,3(2H)-dione The same method as employed in the preparation of Example 41 but starting from trans methyl 1,2,3,4-tetrahydro-1-phenyl-9H-pyrido[3,4-b]indole-3-carboxylate and cyclopropylamine gave after recrystallization from ethanol, the title compound as white crystals m.p.: 250–255° C.

Analysis for $C_{22}H_{19}N_3O_2$: Calculated: C,73.93; H,5.36; N,11.76; Found: C,73.84; H,5.45; N,11.63%.

Example 43

Trans-2-phenethyl-5-phenyl-5,6,11,11a-tetrahydro-1H-imidazo[1',5':1,6]pyrido[3,4-b]indole-1,3(2H)-dione The same method as employed in the preparation of Example 41 but starting from trans methyl 1,2,3,4-tetrahydro-1-phenyl-9H-pyrido[3,4-b]indole-3-carboxylate and phenethylamine gave after recrystallization from diethyl ether, the title compound as white crystals m.p.: 240–242° C.

Analysis for $C_{27}H_{23}N_3O_2$: Calculated: C,76.94; H,5.50; N,9.97; Found: C,77.20; H,5.65; N,10.05%.

Example 44

Trans-5-phenyl-2-(2-pyridylmethyl)-5,6,11,11a-tetrahydro-1H-imidazo[1',5':1,6]pyrido[3,4-b]indole-1,3(2H)-dione The same method as employed in the preparation of Example 41 but starting from trans methyl 1,2,3,4-tetrahydro-1-phenyl-9H-pyrido[3,4-b]indole-3-carboxylate and 2-(aminomethyl) pyridine, gave after recrystallization from methanol, the title compound as white crystals m.p.: 165–175°.

Analysis for $C_{25}H_{20}N_4O_2$: Calculated: C,73.51; H,4.94; N,13.72; Found: C,73.46; H5.29; N,13.84%.

Example 45

Trans-5-phenyl-2-(4-pyridylmethyl)-5,6,11,11a-tetrahydro-1H-imidazo[1',5':1,6]pyrido[3,4-b]indole-1,3(2H)-dione The same method as employed in the preparation of Example 41 but starting from trans methyl 1,2,3,4-tetrahydro-1-phenyl-9H-pyrido[3,4-b]indole-3-carboxylate and 4-(aminomethyl) pyridine, gave after recrystallization from methanol, the title compound as white crystals m.p.: 247–249° C.

Analysis for $C_{25}H_{20}N_4O_2$: Calculated: C,73.51; H,4.94; N,13.72; Found: C,73.41; H,4.98; N,13.62%.

Example 46

Trans-5-(4-methoxyphenyl)-2-(3-pyridylmethyl)-5,6,11,11a-tetrahydro-1H-imidazo[1',5':1,6]pyrido[3,4-b]indole-1,3(2H)-dione The same method as employed in the preparation of Example 41 but starting from Intermediate 4 and 3-(aminomethyl) pyridine, gave after recrystallization from ethanol, the title compound as white crystals m.p.: 160–165° C. Analysis for $C_{26}H_{22}N_4O_3$: Calculated: C,71.22; H,5.06; N,12.78; Found: C,71.12; H,5.15; N,12.59%.

Example 47

Trans-2-(2-dimethylaminoethyl)-5-(4-methoxyphenyl)-5,6,11,11a-tetrahydro-1H-imidazo[1',5':1,6]pyrido[3,4-b]indole-1,3(2H)-dione The same method as employed in the preparation of Example 41 but starting from Intermediate 4 and N,N-dimethyl-ethane-1,2-diamine, gave after recrystallization from ethanol/water, the title compound as pale yellow crystals m.p.: 120–124° C.

Analysis for $C_{24}H_{26}N_4O_3$: Calculated: C,68.88; H,6.26; N,13.39; Found: C,68.91; H,6.43; N,13.23%.

Example 48

Trans-2-(3-dimethylaminopropyl)-5-(4-methoxyphenyl)-5,6,11,11a-tetrahydro-1H-imidazo[1',5':1,6]pyrido[3,4-b]indole-1,3(2H)-dione The same method as employed in the preparation of Example 41 but starting from Intermediate 4 and N,N-dimethyl-propane-1,3-diamine, gave after recrystallization from ethyl acetate/hexane, the title compound as white crystals m.p.: 159–161° C. Analysis for $C_{25}H_{28}N_4O_3$: Calculated: C,69.42; H,6.53; N,12.95; Found: C,68.89; H,6.60; N,12.91%.

Example 49

Trans-2-(2-morpholin-4-yl-ethyl)-5-phenyl-5,6,11,11a-tetrahydro-1H-imidazo[1',5':1,6]pyrido[3,4-b]indole-1,3(2H)-dione The same method as employed in the preparation of Example 41 but starting from trans methyl 1,2,3,4-tetrahydro-1-phenyl-9H-pyrido[3,4-b]indole-3-carboxylate and 2-morpholin-4-yl-ethylamine, gave after recrystallization from ethanol, the title compound as white crystals m.p.: 183–185° C.

Analysis for $C_{25}H_{26}N_4O_3$: Calculated: C,69.75; H,6.09; N,13.01; Found: C,69.68; H,6.17; N,12.80%.

Example 50

Trans-5-(4-methoxyphenyl)-2-[3-(4-methyl-piperazin-1-yl)-propyl]-5,6,11,11a-tetrahydro-1H-imidazo[1',5':1,6]pyrido[3,4-b]indole-1,3(2H)-dione The same method as employed in the preparation of Example 41 but starting from Intermediate 4 and 3-(4-methyl-piperazin-1-yl)-propylamine, gave after recrystallization from ethanol/water, the title compound as white crystals m.p.: 164–168° C.

Analysis for $C_{28}H_{33}N_5O_3$ (0.5 $H_2O$): Calculated: C,67.72; H,6.9; N,14.1; Found: C,67.85; H,6.75; N,14.13%.

Example 51

Trans-5-(4-methoxyphenyl)-2-(2-pyrrolidin-1-yl-ethyl)-5,6,11,11a-tetrahydro-1H-imidazo[1',5':1,6]pyrido[3,4-b]indole-1,3(2H)-dione The same method as employed in the preparation of Example 41 but starting from Intermediate 4 and 2-pyrrolidin-1-yl-ethylamine, gave after recrystallization from ethanol/water, the title compound as white crystals m.p.: 126–130° C. Analysis for $C_{26}H_{28}N_4O_3$: Calculated: C,70.25; H,6.35; N,12.60; Found: C,69.99; H,6.35; N,12.50%.

Example 52

Trans-5-(4-methoxyphenyl)-2-[2-(1-methyl-pyrrolidin-2-yl)-ethyl]-5,6,11,11a-tetrahydro-1H-imidazo[1',5':1,6]pyrido[3,4-b]indole-1,3(2H)-dione The same method as employed in the preparation of Example 41 but starting from Intermediate 4 and 2-(1-methyl-pyrrolidin-2-yl)-ethylamine, gave after recrystallization from methanol, the title compound as white crystals m.p.: 170–180° C.

Analysis for $C_{27}H_{30}N_4O_3$: Calculated: C,70.72; H,6.59; N,12.22; Found: C,70.86; H,6.62; N,12.41%.

Example 53

Trans-5-(4-methoxyphenyl)-5,6,11,11a-tetrahydro-1H-imidazo-[1',5':1,6]pyrido[3,4-b]indole-1,3(2H)-dione A mixture of Intermediate 4 (0.5 g, 1.48 mmol) and urea (0.1 g) was heated at 220° C. for a few minutes. The reaction was then cooled to room temperature and the solid suspended in methanol, filtered then recrystallised from hot methanol to give the title compound as off-white crystals m.p.: 295–305° C.

Analysis for $C_{20}H_{17}N_3O_3$: Calculated: C,69.15; H,4.93; N,12.10; Found: C,68.87; H,4.95; N,12.00%.

Example 54

Cis-5-(4-methoxyphenyl)-5,6,11,11a-tetrahydro-1H-imidazo[1',5':1,6]pyrido[3,4-b]indole-1,3(2H)-dione The same method as employed in the preparation of Example 53 but starting from Intermediate 3 and urea, gave after recrystallization from methanol, the title compound as pale yellow crystals m.p.: 300–310° C.

Analysis for $C_{20}H_{17}N_3O_3$: Calculated: C,69.15; H,4.93; N,12.10; Found: C,68.90; H,4.91; N,11.98%.

Tablets for Oral Administration

A. Direct Compression

| 1. | mg/tablet |
| --- | --- |
| Active Ingredient | 50.0 |
| Crospovidone USNF | 8.0 |
| Magnesium Stearate Ph Eur | 1.0 |
| Anhydrous Lactose | 141.0 |

The active ingredient was sieved and blended with the excipients. The resultant mix was compressed into tablets.

| 2. | mg/tablet |
| --- | --- |
| Active Ingredient | 50.0 |
| Colloidal Silicon Dioxide | 0.5 |
| Crospovidone | 8.0 |
| Sodium Lauryl Sulfate | 1.0 |
| Magnesium Stearate Ph Eur | 1.0 |
| Microcrystalline Cellulose USNF | 139.5 |

The active ingredient was sieved and blended with the excipients. The resultant mix was compressed into tablets.

B. Wet Granulation

| 1. | mg/tablet |
|---|---|
| Active Ingredient | 50.0 |
| Polyvinylpyrrolidone | 150.0 |
| Polyethylene glycol | 50.0 |
| Polysorbate 80 | 10.0 |
| Magnesium Stearate Ph Eur | 2.5 |
| Croscamellose Sodium | 25.0 |
| Colloidal Silicon Dioxide | 2.5 |
| Microcrystalline Cellulose USNF | 210.0 |

The polyvinylpyrrolidone, polyethylene glycol and polysorbate 80 were dissolved in water. The resultant solution was used to granulate the active ingredient. After drying the granules were screened, then extruded at elevated temperatures and pressures. The extrudate was milled and/or screened then was blended with the microcrystalline cellulose, croscarmellose sodium, colloidal silicon dioxide, and magnesium stearate. The resultant mix was compressed into tablets.

| 2. | mg/tablet |
|---|---|
| Active Ingredient | 50.0 |
| Polysorbate 80 | 3.0 |
| Lactose Ph Eur | 178.0 |
| Starch BP | 45.0 |
| Pregelatinized Maize Starch BP | 22.5 |
| Magnesium Stearate BP | 1.5 |

The active ingredient was sieved and blended with the lactose, starch, and pregelatinised maize starch. The polysorbate 80 was dissolved in purified water. Suitable volumes of the polysorbate 80 solution were added and the powders were granulated. After drying, the granules were screened and blended with the magnesium stearate. The granules then were compressed into tablets.

Tablets of other strengths can be prepared by altering the ratio of active ingredient to the other excipients.

Film Coated Tablets

The aforementioned tablet formulations were film coated.

| Coating Suspension | % w/w |
|---|---|
| Opadry white † | 13.2 |
| Purified water Ph Eur | to 100.0* |

† Opadry white is a proprietary material obtaining from Colorcon Limited, UK, which contains hydroxypropyl methylcellulose, titanium dioxide, and triacetin.
*The water did not appear in the final product. The maximum theoretical weight of solids applied during coating was 20 mg/tablet.

The tablets were film coated using the coating suspension in conventional film coating equipment.

Capsules

| 1. | mg/capsule |
|---|---|
| Active Ingredient | 50.0 |
| Lactose | 148.5 |

-continued

| 1. | mg/capsule |
|---|---|
| Polyvinylpyrrolidone | 100.0 |
| Magnesium Stearate | 1.5 |

The active ingredient was sieved and blended with the excipients. The mix was filled into size No. 1 hard gelatin capsules using suitable equipment.

| 2. | mg/capule |
|---|---|
| Active Ingredient | 50.0 |
| Microcrystalline Cellulose | 233.5 |
| Sodium Lauryl Sulfate | 3.0 |
| Crospovidone | 12.0 |
| Magnesium Stearate | 1.5 |

The active ingredient was sieved and blended with the excipients. The mix was filled into size No. 1 hard gelatin capsules using suitable equipment.

Other doses can be prepared by altering the ratio of active ingredient to excipient, the fill weight and if necessary changing the capsule size.

| 3. | mg/capsule |
|---|---|
| Active Ingredient | 50.0 |
| Labrafil M1944CS | to 1.0 ml |

The active ingredient was sieved and blended with the Labrafil. The suspension was filled into soft gelatin capsules using appropriate equipment.

Inhibitory Effect on cGMP-PDE cGMP-PDE activity of compounds of the present invention was measured using a one-step assay adapted from Wells et al., *Biochim. Biophys. Acta,* 384, 430 (1975). The reaction medium contained 50 mM Tris-HCl, pH 7.5, 5 mM magnesium acetate, 250 µg/ml 5'-Nucleotidase, 1 mM EGTA, and 0.15 µM 8-[$H^3$]-cGMP. The enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves typically using concentrations ranging from 10 nM to 10 µM. Tests against other PDE enzymes using standard methodology also showed that compounds of the invention are highly selective for the cGMP-specific PDE enzyme.

cGMP Level Measurements

Rat aortic smooth muscle cells (RSMC), prepared according to Chamley et al., *Cell Tissue Res.,* 177, 503–522 (1977), were used between the 10th and 25th passage at confluence in 24-well culture dishes. Culture media was aspirated and replaced with PBS (0.5 ml) containing the compound tested at the appropriate concentration. After 30 minutes at 37° C., particulates guanylate cyclase was stimulated by addition of ANF (100 nM) for 10 minutes. At the end of incubation, the medium was withdrawn, and two extractions were performed by addition of 65% ethanol (0.25 ml). The two ethanolic extracts were pooled and evaporated until dryness, using a Speed-vac system. cGMP was measured after acetylation by scintillation proximity immunoassay (AMERSHAM). The $EC_{50}$ values are expressed as the dose-giving half of the stimulation at saturating concentrations.

Biological Data

The compounds according to the present invention were typically found to exhibit an $IC_{50}$ value of less than 500 nM and an $EC_{50}$ value of less than 5 μM. In vitro test data for representative compounds of the invention is given in the following table:

TABLE 1

| | In vitro results | |
|---|---|---|
| Example No. | $IC_{50}$ nM | $EC_{50}$ μM |
| 10 | 4 | <1 |
| 26 (cis isomer) | 7 | 0.3 |
| 1 (cis isomer) | <10 | 0.3 |
| 32 | <10 | 0.2 |

The hypotensive effects of compounds according to the invention as identified in Table 2 were studied in conscious spontaneously hypertensive rats (SHRs). The compounds were administered orally at a dose of 5 or 10 mg/kg in a mixture of 5% DMF (dimethylformamide) and 95% olive oil, or i.v. at a dose of 10 mg/kg in a mixture of 40% dimethylformamide, 25% tetraglycol, and 25% glucose serum. Blood pressure was measured from a catheter inserted in the carotid artery and recorded for 5 hours after administration. The results are expressed as Area Under the Curve (AUC from 0 to 5 hours in mmHg.hour) of the fall in blood pressure over time.

TABLE 2

| | In vivo results |
|---|---|
| Example No. | AUC (mmHg · H) |
| 10 | 147 (dosed at 10 mg/kg i.v.) |
| 26 (cis iosmer) | 117 (dosed at 10 mg/kg i.v.) |
| 1 (cis isomer) | 104 (dosed at 5 mg/kg p.o.) |
| 32 | 65 (dosed at 5 mg/kg p.o.) |

Obviously, many modifications and variations of the invention as hereinbefore set forth can be made without departing from the spirit and scope thereof, and, therefore, only such limitations should be imposed as are indicated by the appended claims.

What is claimed is:

1. A combination comprising:
   (a) a compound of having a formula:

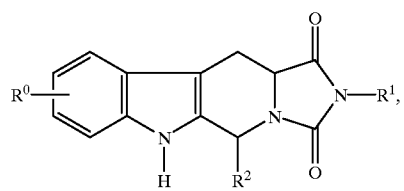

and pharmaceutically acceptable salts and solvates thereof, wherein:
   $R^0$ represents hydrogen, halogen or $C_{1-6}$ alkyl;
   $R^1$ is selected from the group consisting of:
      (i) hydrogen;
      (ii) $C_{1-6}$alkyl optionally substituted by one or more substituents selected from phenyl, halogen, —$CO_2R^a$ and —$NR^aR^b$;
      (iii) $C_{3-6}$cycloalkyl;
      (iv) phenyl; and
      (v) a 5- or 6-membered heterocyclic ring containing at least one heteroatom selected from oxygen, nitrogen and sulphur, and being optionally substituted by one or more $C_{1-6}$alkyl, and optionally linked to the nitrogen atom to which $R^1$ is attached via $C_{1-6}$alkyl;
   $R^2$ is selected from the group consisting of:
      (vi) $C_{3-6}$cycloalkyl;
      (vii) phenyl optionally substituted by one or more substituents selected from —$OR^a$, —$NR^aR^b$, halogen, hydroxy, trifluoromethyl, cyano, and nitro;
      (viii) a 5- or 6-membered heterocyclic ring containing at least one heteroatom selected from oxygen, nitrogen and sulphur; and

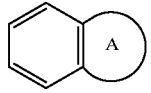

(A) a bicyclic ring attached to the rest of the molecule via one of the benzene ring carbon atoms and A is a 5- or 6-membered heterocyclic ring as defined in point (h); and
   $R^a$ and $R^b$ independently represent hydrogen or $C_{1-6}$alkyl, and
   (b) a second therapeutically active agent,
   for simultaneous, separate, or sequential use in the treatment of a condition where inhibition of a cGMP-specific PDE is of a therapeutic benefit.

2. A pharmaceutical formulation comprising a combination according to claim 1, together with a pharmaceutically acceptable diluent or carrier.

3. The combination of claim 1 wherein the second therapeutically active agent comprises a vasodilator, prostaglandin E1, prostacyclin, an α-adrenergic blocker, a mixed α,β-blocker, an $α_2$-adrenergic blocker, an ACE inhibitor, an NEP inhibitor, a centrally acting dopaminergic agent, a vasoactive intestinal peptide, a calcium channel blocker, a thiazide, or a mixture thereof.

4. The combination of claim 3 wherein the vasodilator is selected from the group consisting of an organic nitrate, an organic nitrite, a thionitrite, a thionitrate, an S-nitrosothiol, a nitrosoprotein, a substituted furoxane, a substituted sydnonimine, a nitrosyl complex compound, nitric oxide, and mixtures thereof.

5. The combination of claim 3 wherein the vasodilator is selected from the group consisting of nitroglycerin, isosorbide dinitrate, pentaerythrityl tetranitrate, isosorbide-5-mononitrate, propatyl nitrate, trolnitrate, nicroandil, mannitol hexanitrate, inositol hexanitrate, N-[3-nitratopivaloyl]-6-cysteine ethyl ester, isoamyl nitrite, S-nitroso-N-acetyl-D, L-penicillamine, 1,2,5-oxadiazole-2-oxide, furazan-N-oxide, molsidomine, mesocarb, an iron nitrosyl compound, sodium nitroprusside, nitric oxide, and mixtures thereof.

6. The combination of claim 1 wherein the second therapeutically active compound is selected from the group consisting of prostaglandin E1, prostacyclin, apomorphine, yohimibine, phentolamine, prazocin, carvedilol, and mixtures thereof.

7. A method of treating a condition where inhibition of a cGMP-specific PDE is of therapeutic benefit, in a human or a nonhuman animal body, comprising administering to said body a therapeutically effective amount of a combination of claim 1.

8. The method of claim 7 wherein the cGMP-specific PDE is PDE5.

9. The method of claim 7 wherein the condition is erectile dysfunction in a male or female animal.

10. The method of claim 9 wherein the male or female animal is a human male or female animal.

11. The method of claim 7 wherein the treatment is an oral treatment.

12. A method of treating stable angina, unstable angina, variant angina, hypertension, pulmonary hypertension, chronic obstructive pulmonary disease, acute respiratory distress syndrome, malignant hypertension, pheochromocytoma, congestive heart failure, acute renal failure, chronic renal failure, atherosclerosis, a condition of reduced blood vessel patency, a peripheral vascular disease, a vascular disorder, thrombocythemia, an inflammatory disease, myocardial infarction, stroke, bronchitis, chronic asthma, allergic asthma, allergic rhinitis, glaucoma, peptic ulcer, a gut motility disorder, postpercutaneous transluminal coronary angioplasty, carotid angioplasty, post-bypass surgery graft stenosis, osteoporosis, preterm labor, benign prostatic hypertrophy, or irritable bowel syndrome, in a human or nonhuman animal body, said method comprising administering to said body a therapeutically effective amount of a combination of claim 1.

13. The method of claim 12 wherein the compound is administered orally.

* * * * *

UNITED STATES PATENT AND TRADEMARK OFFICE
CERTIFICATE OF CORRECTION

PATENT NO.      : 6,143,757
DATED           : November 7, 2000
INVENTOR(S)     : Alain Claude-Marie Daugan et al.

It is certified that error appears in the above-identified patent and that said Letters Patent is hereby corrected as shown below:

Title page,
Item [56], References Cited, OTHER PUBLICATIONS, "Martinez-Pineiro et al." reference, "1992" should be -- (1993) --

Column 4,
Line 36, "-ethyl]5, 6, 11, 11a-" should be -- -ethyl]-5, 6, 11, 11a- --

Column 5,
Line 13, "Tetrohydro" should be -- tetrahydro --

Column 11,
Line 21, "on other" should be -- or other --

Column 15,
Line 34, "(ppm)" should be -- (ppm) : --

Column 16,
Lines 2 and 10, "pyrido-[3,4-b]" should be -- pyrido[3,4-b] --

Column 17,
Line 33 and 36, "pyrido-[3,4-b]" should be -- pyrido[3,4-b] --

Column 18,
Line 44, "pyrido-[3,4-b]" should be -- pyrido[3,4-b] --

Column 19,
Line 25, "pyrido-[3,4-b]" should be -- pyrido[3,4-b] --

Column 20,
Line 65, "dione" should be -- dione and --

Column 21,
Lines 38-39, "-1H-[1',5':1,6]" should be -- -1H-imidazo[1',5':1,6] --

Column 22,
Line 57, "recrystallization toluene," should be -- recrystallization from toluene, --

Column 23,
Line 51, "phenyl-5 6,11,11a-" should be -- phenyl-5,6,11,11a- --

UNITED STATES PATENT AND TRADEMARK OFFICE
CERTIFICATE OF CORRECTION

PATENT NO. : 6,143,757
DATED : November 7, 2000
INVENTOR(S) : Alain Claude-Marie Daugan et al.

It is certified that error appears in the above-identified patent and that said Letters Patent is hereby corrected as shown below:

Column 24,
Line 26, "Na2SO4" should be -- $Na_2SO_4$ --

Column 26,
Line 22, "imidazo-[1',5':1,6]" should be -- imidazo[1',5':1,6] --

Column 27,
Line 10, "Croscamellose" should be -- Croscarmellose --

Signed and Sealed this

Twenty-seventh Day of April, 2004

JON W. DUDAS
*Acting Director of the United States Patent and Trademark Office*